United States Patent
Kaneko et al.

(10) Patent No.: US 10,527,615 B2
(45) Date of Patent: Jan. 7, 2020

(54) ANTIGEN DETECTION METHOD WHICH USES LECTIN AND COMPRISES ENZYME TREATMENT STEP

(71) Applicant: KONICA MINOLTA, INC., Chiyoda-ku, Tokyo (JP)

(72) Inventors: Tomonori Kaneko, Sagamihara (JP); Youichi Ide, Wako (JP)

(73) Assignee: KONICA MONOLTA, INC., Tokyo (JP)

(*) Notice: Subject to any disclaimer, the term of this patent is extended or adjusted under 35 U.S.C. 154(b) by 0 days.

(21) Appl. No.: 14/396,646

(22) PCT Filed: Apr. 15, 2013

(86) PCT No.: PCT/JP2013/061203
§ 371 (c)(1),
(2) Date: Oct. 23, 2014

(87) PCT Pub. No.: WO2013/161614
PCT Pub. Date: Oct. 31, 2013

(65) Prior Publication Data
US 2015/0140571 A1    May 21, 2015

(30) Foreign Application Priority Data
Apr. 27, 2012  (JP) .................. 2012-102947

(51) Int. Cl.
*C12Q 1/34* (2006.01)
*G01N 33/566* (2006.01)
*G01N 33/53* (2006.01)

(52) U.S. Cl.
CPC .................. *G01N 33/566* (2013.01)

(58) Field of Classification Search
CPC .......... G01N 33/53; G01N 33/579; C12Q 1/34
See application file for complete search history.

(56) References Cited

U.S. PATENT DOCUMENTS

| 5,591,589 A | 1/1997 | Katoh et al. |
| 5,866,433 A | 2/1999 | Schalkhammer et al. |

(Continued)

FOREIGN PATENT DOCUMENTS

| EP | 0399464 A1 | 5/1990 |
| EP | 653640 A1 | 5/1995 |

(Continued)

OTHER PUBLICATIONS

Moira et al., "Lectins: tools for the molecular understanding of the glycocode," published Apr. 11, 2005.*

(Continued)

*Primary Examiner* — Tracy Vivlemore
*Assistant Examiner* — Nam P Nguyen
(74) *Attorney, Agent, or Firm* — Holtz, Holtz & Volek PC

(57) ABSTRACT

An antigen detection method detects an antigen having a specific sugar chain in a sample with a lectin that binds to plural kinds of sugar chains including the specific sugar chain. The detection method includes: a first step of bringing the lectin into contact with the sample; a second step of bringing a glycohydrolase capable of cleaving at least one kind of sugar chain to which the lectin can bind into contact with the sample, the at least one kind of sugar chain excluding the specific sugar chain among the plural kinds of sugar chains; and a step of detecting the antigen bound with the lectin after the first and second steps.

18 Claims, 4 Drawing Sheets

(56) References Cited

U.S. PATENT DOCUMENTS

| | | | |
|---|---|---|---|
| 8,039,609 | B2 | 10/2011 | Missailidis et al. |
| 8,883,977 | B2 | 11/2014 | Nishimura et al. |
| 9,874,558 | B2 | 1/2018 | Isoda et al. |
| 2004/0147033 | A1 | 7/2004 | Shriver et al. |
| 2005/0042209 | A1 | 2/2005 | Kufe et al. |
| 2005/0180997 | A1 | 8/2005 | Benita et al. |
| 2008/0074671 | A1 | 3/2008 | Ohtsuka et al. |
| 2008/0293147 | A1* | 11/2008 | Machida ............ G01N 33/566 436/64 |
| 2009/0061455 | A1 | 3/2009 | Sankaran et al. |
| 2009/0286854 | A1 | 11/2009 | Missailidis et al. |
| 2010/0087363 | A1* | 4/2010 | Rubinstein ........... C07K 14/705 514/21.2 |
| 2010/0216163 | A1* | 8/2010 | Kuballa et al. .............. 435/7.9 |
| 2010/0272707 | A1 | 10/2010 | Bay et al. |
| 2011/0129849 | A1* | 6/2011 | Zhang ............. G01N 33/57434 435/7.1 |
| 2011/0294141 | A1 | 12/2011 | Yamashita et al. |
| 2012/0065089 | A1 | 3/2012 | Kuno et al. |
| 2012/0282612 | A1 | 11/2012 | Yamashita et al. |
| 2013/0045543 | A1 | 2/2013 | Nishimura et al. |
| 2013/0116142 | A1 | 5/2013 | Watson et al. |
| 2014/0162888 | A1 | 6/2014 | Kuslich et al. |
| 2014/0170772 | A1* | 6/2014 | Ide et al. ...................... 436/501 |
| 2014/0186853 | A1 | 7/2014 | Yamashita et al. |
| 2015/0140571 | A1 | 5/2015 | Kaneko et al. |
| 2016/0138118 | A1 | 5/2016 | Yamashita et al. |
| 2016/0305960 | A1 | 10/2016 | Yamashita et al. |
| 2017/0122940 | A1* | 5/2017 | Kaneko ............ G01N 33/54393 |

FOREIGN PATENT DOCUMENTS

| | | |
|---|---|---|
| EP | 2395357 A1 | 12/2011 |
| JP | 61292062 A | 12/1986 |
| JP | H03073852 A | 3/1991 |
| JP | 04130274 A | 5/1992 |
| JP | 07191027 A | 7/1995 |
| JP | 2001255325 A | 9/2001 |
| JP | 3562912 B2 | 9/2004 |
| JP | 2006112834 A | 4/2006 |
| JP | 2008102117 A | 5/2008 |
| JP | 2008529967 A | 8/2008 |
| JP | 2009053195 A | 3/2009 |
| JP | 2009535051 A | 10/2009 |
| JP | 2010060293 A | 3/2010 |
| JP | 2010127827 A | 6/2010 |
| JP | 2010145272 A | 7/2010 |
| JP | 2011080935 A | 4/2011 |
| JP | 2011137754 A | 7/2011 |
| JP | 2012185172 A | 9/2012 |
| JP | 2012255736 A | 12/2012 |
| JP | 5413544 B1 | 4/2013 |
| JP | 2013076666 A | 4/2013 |
| JP | 2013526852 A | 6/2013 |
| JP | 5231247 B2 | 7/2013 |
| JP | 2013253866 A | 12/2013 |
| WO | 2005064333 A1 | 7/2005 |
| WO | 2007129114 A2 | 11/2007 |
| WO | 2010074265 A1 | 7/2010 |
| WO | 2010090264 A1 | 8/2010 |
| WO | 2010100862 A1 | 9/2010 |
| WO | 2010123073 A1 | 10/2010 |
| WO | 2010134592 A1 | 11/2010 |
| WO | 2011052244 A1 | 5/2011 |
| WO | 2011135869 A1 | 11/2011 |
| WO | WO-2011161150 A1 * | 12/2011 |
| WO | 2012173228 A1 | 12/2012 |
| WO | 2013054281 A1 | 4/2013 |
| WO | 2013070089 A1 | 5/2013 |
| WO | 2014025013 A1 | 2/2014 |
| WO | 2014087802 A1 | 6/2014 |

OTHER PUBLICATIONS

Fukushima et al., "alpha-1,2-Fucosylated and beta-N-actegalactosaminylated prostate-specific antigen as an efficient marker of prostatic cancer," published Dec. 9, 2009.*

INTECH, Affinity Chromatography, retrieved from http://cdn.intechopen.com/pdfs-wm/33048.pdf, published online Mar. 21, 2012.*

Takeya et al., "Presence of B-linked GalNAc residues on N-glycans of human throglobulin", Life Science, vol. 80, pp. 538-545, published 2007.*

Medicago <http://www.medicago.se/lens-culinaris-lectin-lcalch>, print retrieved Dec. 26, 2018. (Year: 2018).*

Vector <https://vectorlabs.com/unconjugated-aleuria-aurantia-lectin-aal.html>, print retrieved Dec. 26, 2018 (Year: 2018).*

GeneTex <http://www.genetex.com/WGA-Lectin-Biotin-GTX01501.html>, print retrieved Dec. 26, 2018 (Year: 2018).*

Weatherman et al., "Specificity of C-glycoside complexation by mannose/glucose specific lectins", Biochemistry, vol. 35(11), pp. 3619-3624, published Mar. 19, 1996, (Abstract Only). (Year: 1996).*

International Preliminary Report on Patentability (IPRP) including Written Opinion, dated Oct. 28, 2014, issued in International Application No. PCT/JP2013/061203.

International Search Report (ISR) dated Jul. 9, 2013 issued in International Application No. PCT/JP2013/061203.

K. Yamashita, et al., "Carbohydrate Structures of Nonspecific Cross-reacting Antigen-2, a Glycoprotein Purified from Meconium as an Antigen Cross-reacting with Anticarcinoembryonic Antigen Antibody", Journal of Biol. Chem., vol. 264, 30, Oct. 25, 1989, pp. 17873-17881 (in English).

K. Yamashita, et al., "Structural Studies of the Carbohydrate Moieties of Carcinoembryonic Antigens", Cancer Research, 47, Jul. 1, 1987, pp. 3451-3459 (in English).

K. Yamashita, et al., "Sugar Chains of Human Cord Serum α-Fetoprotein: Characteristics of N-linked Sugar Chains of Glycoproteins Produced in Human Liver and Hepatocellular Carcinomas", Cancer Research, 53, Jul. 1, 1993, pp. 2970-2975 (in English).

Extended European Search Report dated Aug. 28, 2015, issued in counterpart European Application No. 13780782.2.

Fukushima, et al., "α1,2-Fucosylated and β-N-acetylgalactosaminylated prostate-specific antigen as an efficient marker of prostatic cancer", Glycobiology, vol. 20, No. 4, pp. 452-460, Apr. 1, 2010.

Takeya, et al., "Presence of β-linked GalNAc residues on N-glycans of human thyroglobulin", Life Sciences, Pergamon Press, vol. 80, No. 6, pp. 538-545, Jan. 6, 2007.

Naritmatsu, et al., "A strategy for discovery of cancer glycobiomarkers in serum using newly developed technologies for glycoproteomics", The FEBS Journal; Jan. 2010, pp. 95-105, vol. 277, No. 1.

Extended European Search Report (EESR) dated Jul. 7, 2017 issued in European Application No. 13900337.0.

Burke, et al., "Characterization of MUC1 glycoprotein on prostate cancer for selection of targeting molecules", International Journal of Oncology, vol. 29, Issue 1, Jul. 2006, pp. 49-545.

Devine, et al., "Prostate-specific antigen (PSA) and cancer-associated serum antigen (CASA) in distinguishing benign and malignant prostate diesase", International Journal of Biological Markers, vol. 10, No. 4, Jan. 1995, pp. 221-225.

Matsuda, et al., "Wisteria floribunda Agglutinin-Positive Mucin 1 Is a Sensitive Biliary Marker for Human Cholangiocarcinoma", Hepatology, 2010, vol. 52, No. 1, pp. 174-182.

Mislovicova, et al., "Lectinomics I. Relevance of exogenous plant lectins in biomedical diagnostics", Biologia, vol. 64, No. 1, 2009, pp. 1-19.

Xiang, et al., "Tumor infiltrating dendritic cells and Mucin1 gene expression in benign prostatic hyperplasia and prostate cancer", National Journal of Andrology, 2003, vol. 9, No. 7, pp. 497-500, Abstract.

Devine, et al., "Serum Mucin Antigens CASA and MSA in Tumors of the Breast, Ovary, Lung, Pancreas, Bladder, Colon, and Prostate", Cancer, vol. 72, No. 6, Sep. 15, 1993, pp. 2007-2015.

(56) References Cited

OTHER PUBLICATIONS

Falsaperla, et al., "Role of Ca 15-3 in patients with biochemically suspected prostate cancer and multiple negative ultrasound-guided prostate biopsies", Prostate Cancer and Prostatic Diseases, vol. 6, No. 1, Jan. 1, 2003, pp. 45-49.
Ohyabu, et al., "An Essential Epitope of Anti-MUC1 Monoclonal Antibody KL-6 Revealed by Focused Glycopeptide Library", Journal of the American Chemical Society, vol. 131, No. 47, Dec. 2, 2009, pp. 17102-17109.
Rubenstein et al., "Application of Immunohistologic Staining to Develop a Malignant Index to Aid in Distinguishing Benign From Malignant Prostatic Tissue", The Prostate, vol. 14, No. 1, Wiley-Liss, New York, NY, Jan. 1, 1989, pp. 383-388.
Office Action (Non-Final Rejection) dated Jun. 30, 2017 issued in U.S. Appl. No. 15/108,283.
Japanese Office Action (and an English translation thereof) dated Sep. 5, 2017 issued in Japanese Application No. 2015-554444.
Devine, et al., "Serum Mucin Antigens CASA and MSA in Tumors of the Breast, Ovary, Lung, Pancreas, Bladder, Colon, and Prostate", Cancer, vol. 72, No. 6, Sep. 15, 2003, pp. 2007-2015.
Rubinstein, et al., "Application of Immunohistologic Staining to Develop a Malignant Index to Aid in Distinguishing Benign From Malignant Prostatic Tissue", The Prostate, vol. 14, No. 1, Wiley-Liss, New York, NY, Jan. 1, 1989, pp. 383-388.
Office Action (Non-Final Rejection) dated Dec. 12, 2017 issued in related U.S. Appl. No. 15/108,286.
Japanese Office Action (and English translation thereof) dated Sep. 12, 2017 issued in Japanese Application No. 2015-554445.
Office Action (Requirement for Restriction) dated Jul. 19, 2017 issued in U.S. Appl. No. 15/108,286.
Office Action (Final Rejection) dated Jun. 27, 2018 issued in related U.S. Appl. No. 15/108,286.
European Office Action dated Jun. 28, 2018 issued in European Application No. 13900340.4.
European Office Action dated Jun. 21, 2016, issued in counterpart European Application No. 13780782.2.
European Office Action dated Nov. 18, 2016, issued in counterpart European Application No. 13780782.2.
European Office Action dated Sep. 3, 2018 issued in European Application No. 13900337.0.
Office Action (Advisory Action) dated Aug. 15, 2018 issued in related U.S. Appl. No. 15/108,283.
Office Action (Final Rejection) dated May 23, 2018 issued in related U.S. Appl. No. 15/108,283.
Office Action (Restriction Requirement) dated Mar. 16, 2017 issued in related U.S. Appl. No. 15/108,283.
Office Action (withdrawn Final Rejection) dated Apr. 20, 2018 issued in related U.S. Appl. No. 15/108,283.
Rabiau, et al., "Immunohistochemical Staining of Mucin 1 in Prostate Tissues", In Vivo 23(2); 203-207, Mar.-Apr. 2009.
International Search Report (ISR) including Written Opinion dated Mar. 18, 2014, issued in International Application No. PCT/JP2013/085115.
International Search Report (ISR) including Written Opinion dated Mar. 4, 2014, issued in International Application No. PCT/JP2013/085116.
Extended European Search Report (EESR) (in English) dated May 10, 2017 issued in European Application No. 13900340.4.
Written Opinion of the International Searching Authority dated Aug. 4, 2015 (and English translation thereof) issued in International Application No. PCT/JP2015/065731.
European Office Action dated Sep. 5, 2018 issued in European Application No. 15809575.2.
Extended European Search Report (EESR) dated Dec. 20, 2017 issued in European Application No. 15809575.2.
International Search Report dated Aug. 4, 2015 issued in International Applicaiton No. PCT/JP2015/065731.
Japanese Office Action dated Sep. 18, 2018 (and English translation thereof) issued in Japanese Application No. 2016-529213.
Ho, et al., "Carbohydrate binding activities of Bradyrhizobium japonicum III, Lectin expression, bacterial binding, and nodulation efficiency", The Plant Journal, vol. 5, No. 6, Jun. 1, 1994, pp. 873-884.
U.S. Office Action dated Oct. 12, 2018 issued in U.S. Appl. No. 15/320,118.
U.S. Office Action (Final Rejection) dated Jun. 21, 2019 issued in U.S. Appl. No. 15/320,118.

\* cited by examiner

[Fig.1a]
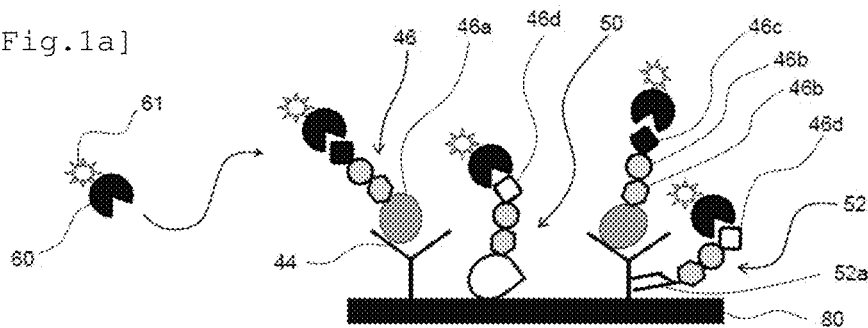
[Fig.1b]
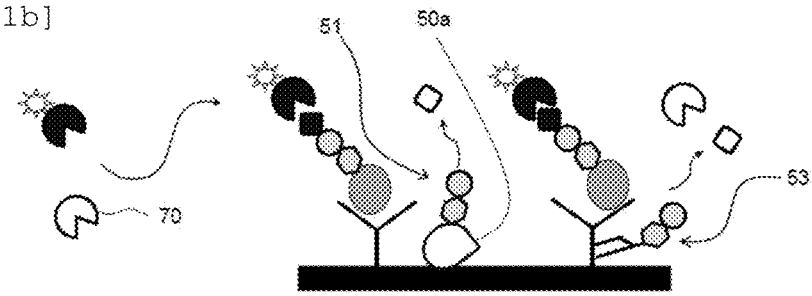
[Fig.2]
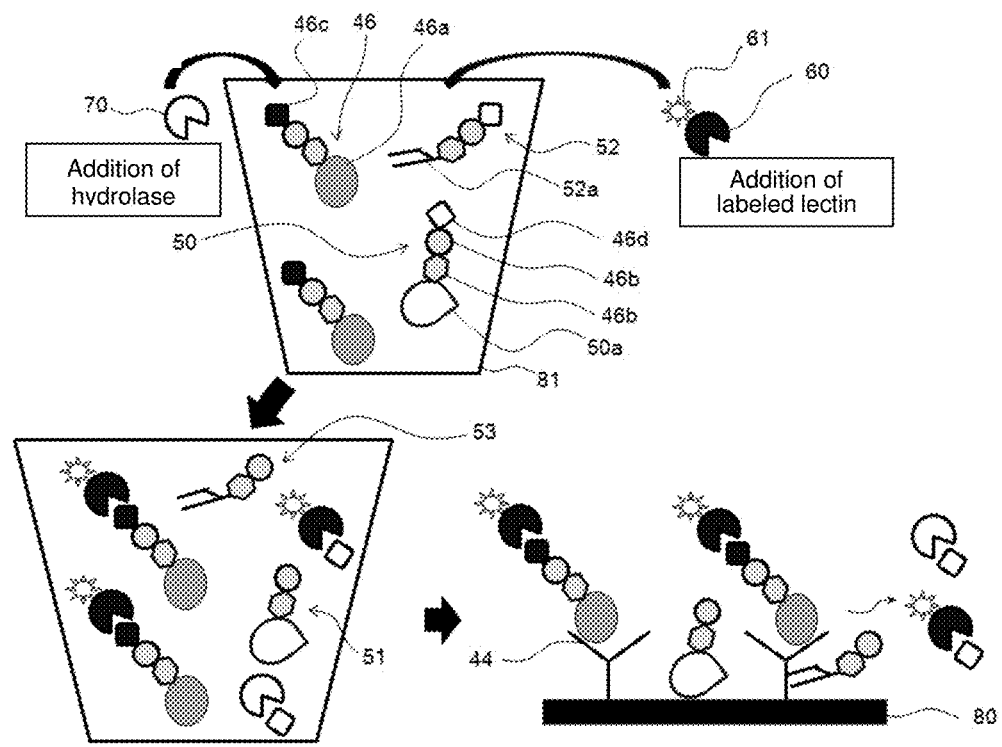

[Fig.3]
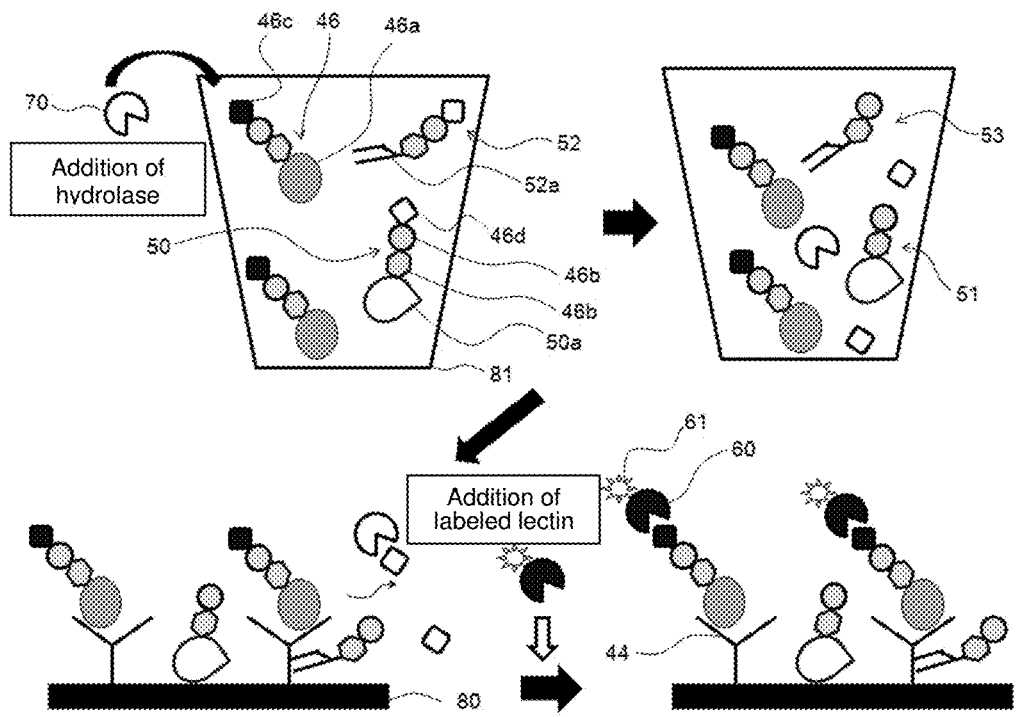
[Fig.4]
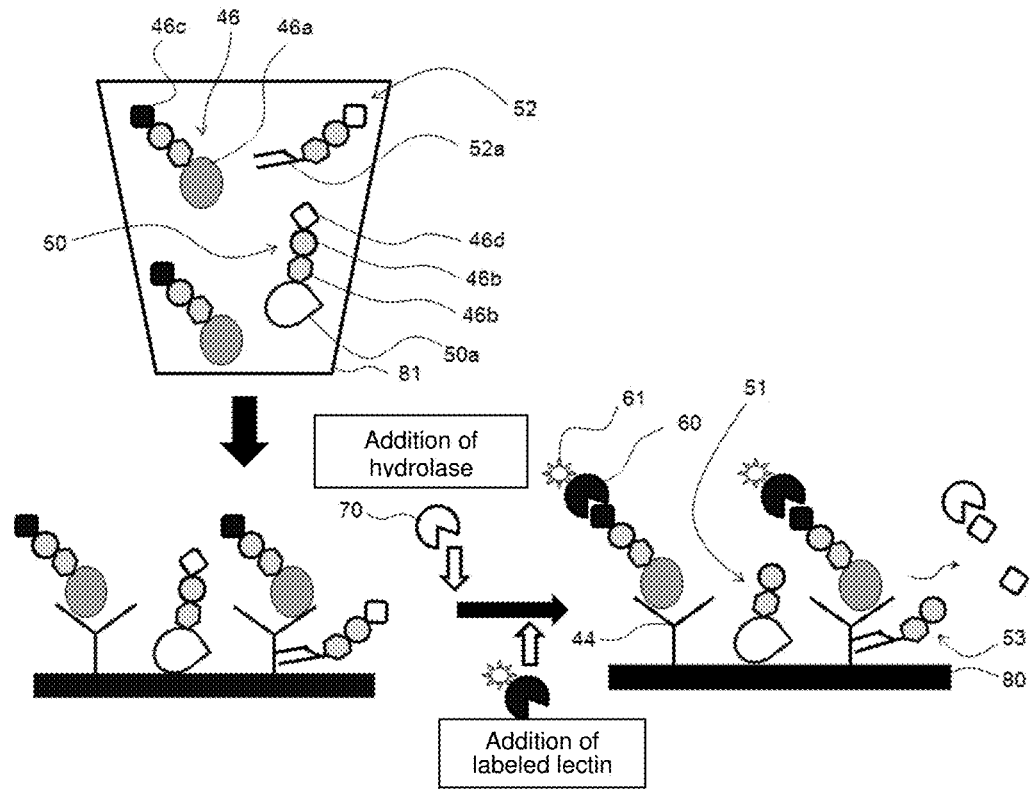

[Fig.5]
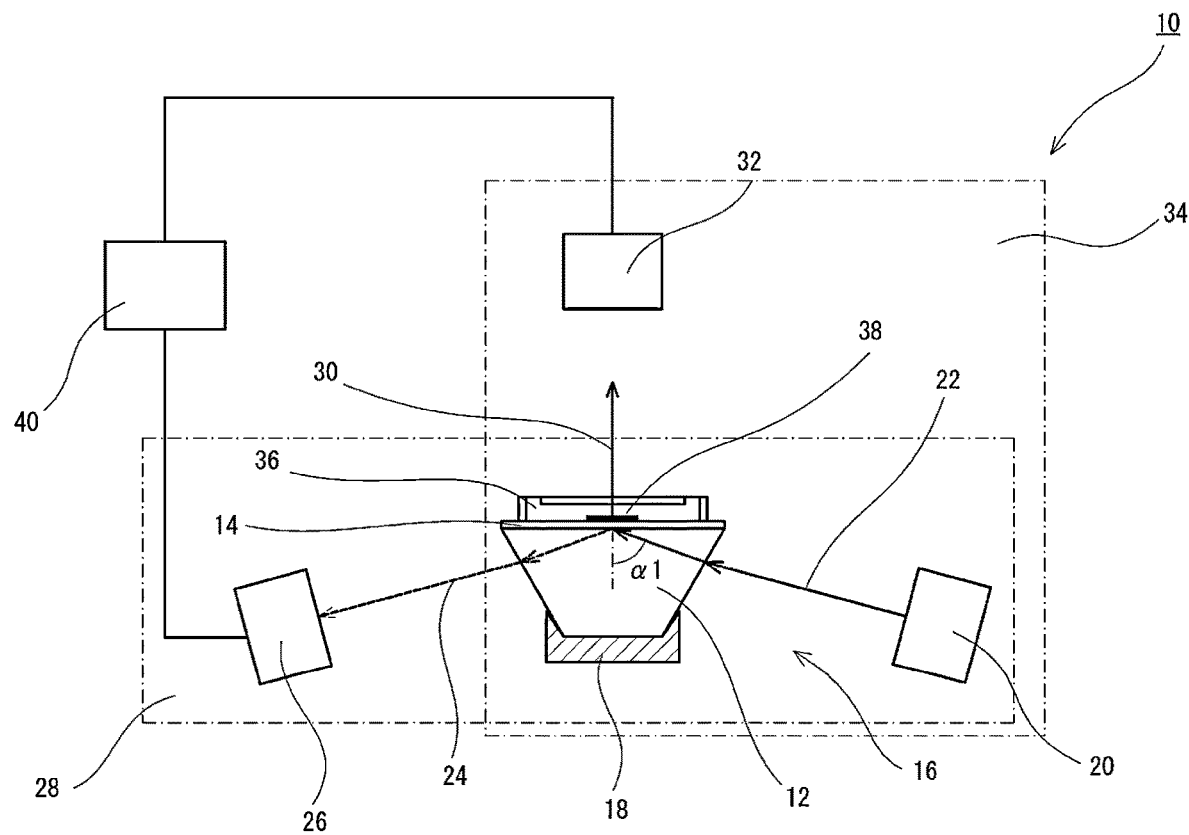
[Fig.6]
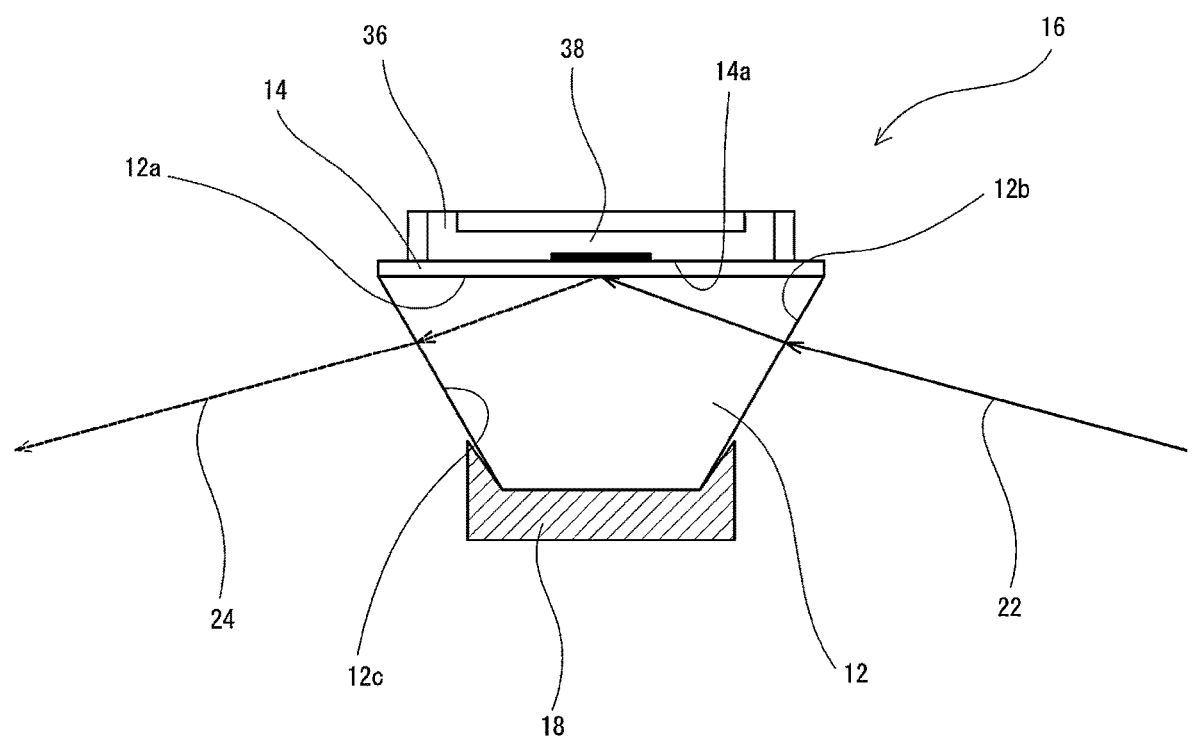

[Fig.7]
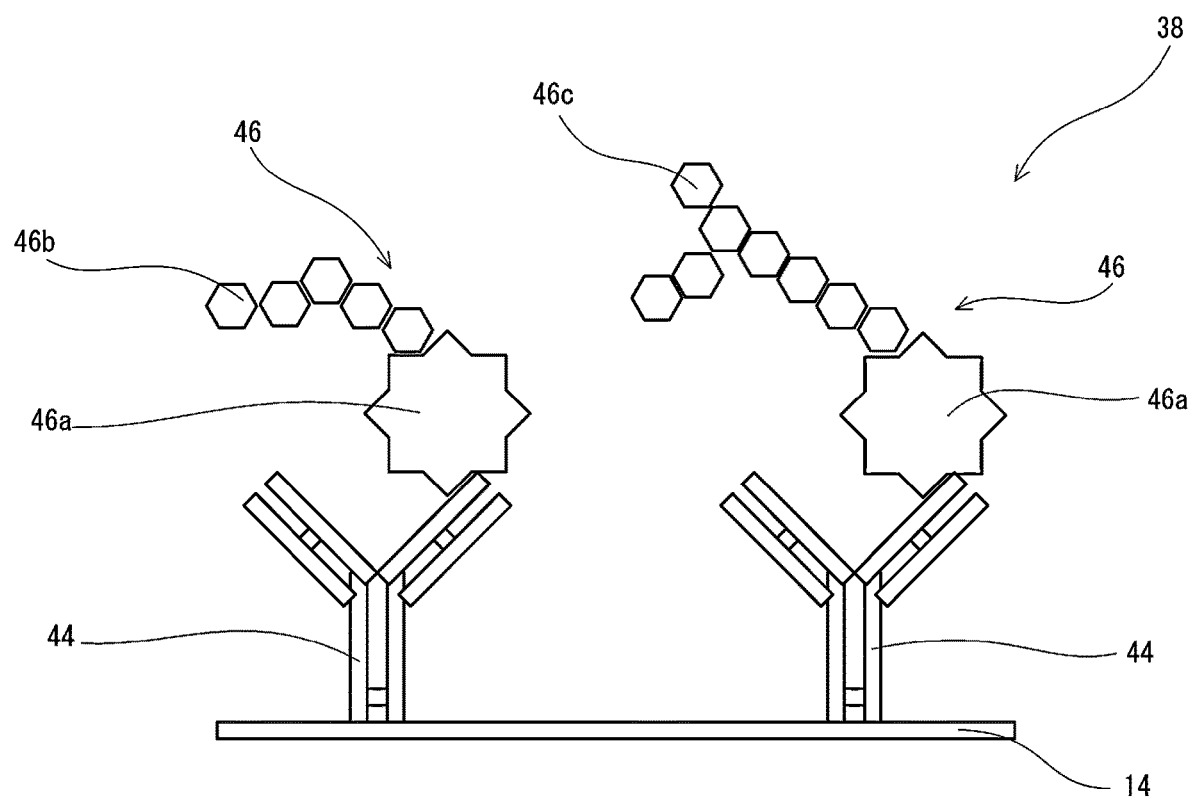
[Fig.8]
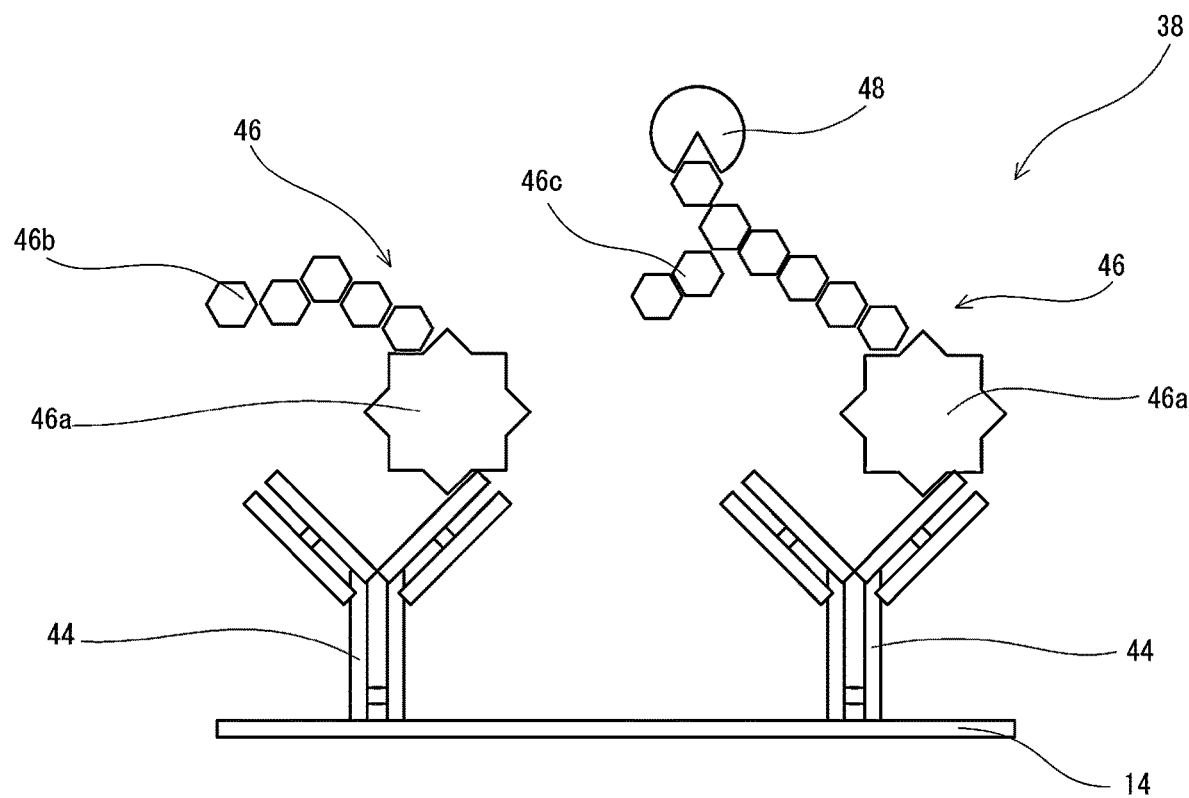

ANTIGEN DETECTION METHOD WHICH USES LECTIN AND COMPRISES ENZYME TREATMENT STEP

TECHNICAL FIELD

The present invention relates to an antigen detection method using a lectin. More particularly, the present invention relates to a high-sensitivity and low-noise antigen detection method using a lectin, the method comprising the step of subjecting a sample to an enzyme treatment.

BACKGROUND ART

In order to allow proteins assuming a principal role in the biological life functions to orderly exert their functions in the cellular world, post-translation modifications including glycosylation play an extremely important role. In recent years, it has been gradually revealed that most in vivo proteins undergo modifications with sugar chains and that those sugar chains attached to proteins play important roles in various aspects of biological phenomena such as viral infection, protozoan parasitism and infection, binding of toxins, binding of hormones, fertilization, development and differentiation, protein stability, cancer cell metastasis, and apotosis.

It is known that even those proteins having an identical amino acid sequence (proteins with the same name) are modified with a wide variety of sugar chains and the structures of these sugar chains vary depending on the condition of the protein-producing cells.

The relationships between such changes in sugar chains and diseases have also been gradually elucidated and the findings have been applied to, for example, such methods of identifying hepatoma by fraction measurement of α-fetoprotein (AFP) sugar chains as disclosed in Patent Document 1 and Non-patent Document 1, such methods of identifying prostate adenocarcinoma by fraction measurement of prostate-specific antigen (PSA) sugar chains as disclosed in Patent Document 2, and such methods of identifying adenocarcinoma by fraction measurement of carcinoembryonic antigen (CEA) sugar chains as disclosed in Non Patent Documents 2 and 3.

For specific detection of a sugar chain on a glycoprotein, proteins called lectins that are capable of specifically recognizing, binding to and cross-linking a sugar chain are widely utilized. This is because it is very difficult to prepare an antigen against a sugar chain and such an antigen is hardly available.

Lectins are inexpensive and available in a large amount. In addition, lectins show excellent protein stability and can thus be stored over a prolonged period. However, lectins have such drawbacks of having lower binding activity and specificity than antibodies.

For example, N-acetylgalactosamine is known as a main binding sugar chain in *Wisteria floribunda* lectin (WFA); however, since N-acetylgalactosamine shows slight binding with galactose, it may non-specifically react with a galactose residue if present in a reaction system.

As a method of simply and quantitatively analyzing a sugar chain on a particular protein using a lectin having such a property, a sandwich assay using an antibody against a protein and a lectin is exemplified.

However, although this technique is effective when the subject protein is purified to a certain extent, since it shows markedly reduced performance in terms of sensitivity and quantitative capacity in a system that contains a large amount of contaminants, such as glycoproteins and glycolipids that are not measurement subjects and included in blood, urine and the like to be used as a sample in ordinary disease diagnosis, it is very difficult to perform an analysis using this technique. Accordingly, this technique is utilized only in serum diagnosis and the like of limited items in which the serum concentration of subject protein is extremely high (about several μg/mL).

As measures for reducing the effects of such contaminants, the use of a blocking agent which inhibits adsorption of serum contaminants to the surface of an antibody-immobilized support (Patent Document 3), the addition of an adsorbent which allows non-specific substances to be adsorbed in advance (Patent Documents 4 and 5) and the use of a washing solution capable of efficiently removing molecules adsorbing to a support (Patent Document 3) have been examined.

Here, as blocking agents, for example, bovine serum albumin (BSA) and casein are known, and synthetic macromolecular materials are also used in some cases, An absorbent for non-specific substances is a molecular which is capable of binding with molecules that inhibit antigen-antibody reaction and cause noise generation and removing such molecules from a reaction system. As such an absorbent, macromolecules and sugar chain complexes such as glycosaminoglycan and heparin may be used. As for a washing solution, the composition thereof has been examined and there is also a report of a case where the effects of salt strength and various surfactants are investigated (Patent Document 3).

However, it is an extremely rare case where these background-suppressing measures show a drastic effect in quantitative analysis using a lectin for detection, and there is also a problem that the search and examination of subject-suitable blocking agent require tremendous man-hours.

CITATION LIST

Patent Literature

[Patent Literature 1] JP S61-292062 A
[Patent Literature 2] WO 2010/090264
[Patent Literature 3] JP 2010-127827 A
[Patent Literature 4] JP 2009-53195 A
[Patent Literature 5] JP 2010-60293 A

Non Patent Literature

[Non Patent Literature 1] Sugar Chains of Human Cord Serum α-Fetoprotein: Characteristics of N-linked Sugar Chains of Glycoproteins Produced in Human Liver and Hepatocellular Carcinomas, K. Yamashita et al., Cancer Res., 53, 1 (1993)
[Non Patent Literature 2] Carbohydrate Structures of Non-specific Cross-reacting Antigen-2, a Glycoprotein Purified from Meconium as an Antigen Cross-reacting with Anticarcinoembryonic Antigen Antibody, K, Yamashita et al., Biol, Chem., 264, 17873 (1989)
[Non Patent Literature 3] Structural Studies of the Carbohydrate Moieties of Carcinoembryonic Antigens, K. Yamashita et al., Cancer Res., 47, 3451 (1987)

SUMMARY OF INVENTION

Technical Problem

Objects of the present invention are: to provide an antigen detection method which can improve the detection sensitivity and quantitative performance for a sugar chain on an antigen to be detected with a lectin by a simple technique (simple constitution) in an antigen detection system using a lectin; and to provide a detection kit.

Solution to Problem

The present inventors intensively studied to solve the above-described problems and discovered that high background (noise) in a measurement system using a lectin is attributed to that, since a lectin used for detection has a certain range in its sugar chain recognition, the lectin may also bind to glycoproteins and glycolipids which are not detection subjects and are generated in certain amounts even when a known treatment method using a blocking agent or the like is performed, being non-specifically bound to a support, an antigen-binding molecule (e.g., antibody) and the like. Based on this new finding, the present inventors discovered that suppression of background and increase in the sensitivity can be attained by cleaving at least one sugar chain excluding the target sugar chain with hydrolase, thereby completing the present invention. That is, in one aspect of the present invention, in order to realize at least one of the above-described objects, the present invention includes the following matters.

[1] A method of detecting an antigen having a particular sugar chain in a sample with a lectin that binds to plural kinds of sugar chains including the particular sugar chain, the method comprising: a first step of bringing the lectin into contact with the sample; a second step of bringing a glycohydrolase capable of cleaving at least one kind of sugar chain to which the lectin can bind into contact with the sample, the at least one kind of sugar chain excluding the particular sugar chain among the plural kinds of sugar chains; a fourth step of detecting the antigen bound with the lectin after the first and second steps.

[2] A kit for detecting an antigen having a particular sugar chain, the kit comprising: a reagent which comprises a lectin that binds to plural kinds of sugar chains including the particular sugar chain; a reagent which comprises a glycohydrolase capable of cleaving at least one kind of sugar chain to which the lectin can bind, the at least one kind of sugar chain excluding the particular sugar chain among the plural kinds of sugar chains; and a reagent which comprises a molecule that binds to an antigen having the particular sugar chain.

FIG. 1 provides conceptual diagrams showing one example of the means for solving the problems according to the present invention. In FIG. 1, a lectin that binds to plural kinds of sugar chains including a particular sugar chain recognizes both a particular sugar chain (46c) and a sugar chain (46d) which excludes the particular sugar chain and to which the lectin can bind. For example, in a case where WFA lectin is used for a PSA antigen, the particular sugar chain (46c) corresponds to N-acetyl-D-galactosamine (GalNAc) and the sugar chain (46d) which excludes the particular sugar chain and to which the lectin can bind, corresponds to galactose (Gal).

Advantageous Effects of Invention

According to the present invention, an antigen detection method which can suppress an increase in the background of a measurement system and improve the detection sensitivity and quantitative performance for a sugar chain on an antigen to be detected with a lectin by a simple technique (simple constitution) in an antigen detection system using a lectin, as well as a detection kit can be provided.

Further, since the above-described effects can be attained only by incorporating an enzyme into a reagent in a sandwich assay system, the antigen detection method of the present invention is a simple technique (simple constitution) and can be effectively applied to diagnosis scene.

BRIEF DESCRIPTION OF THE DRAWINGS

FIG. 1 provides conceptual diagrams showing an example of the mechanism of background generation in detection of an antigen with a lectin (FIG. 1a) and an example of the means for suppressing background and increasing the sensitivity according to the present invention (FIG. 1b).

FIG. 2 is a conceptual diagram showing one embodiment of the method according to the present invention, wherein a hydrolase and a lectin are brought into contact with a sample and the sample is then brought into contact with a support on which an antibody is solid-phased.

FIG. 3 is a conceptual diagram showing one embodiment of the method according to the present invention, wherein a hydrolase is brought into contact with a sample and the sample is subsequently brought into contact with a support on which an antibody is solid-phased and then with a lectin.

FIG. 4 is a conceptual diagram showing one embodiment of the method according to the present invention, wherein, after bringing a sample into contact with a support on which an antibody is solid-phased, a hydrolase and then a lectin are brought into contact with the sample.

FIG. 5 is a drawing which schematically shows the outline of a quantitative measurement apparatus for illustrating the method of quantitatively measuring a specific analyte according to the present invention.

FIG. 6 is a partially enlarged view of the quantitative measurement apparatus shown in FIG. 5.

FIG. 7 is an enlarged drawing which schematically shows a sensor section 38 after transfer of an antigen to be detected (analyte) 46.

FIG. 8 is an enlarged drawing which schematically shows the sensor section 38 after transfer of fluorescently-labeled lectin 48.

DESCRIPTION OF EMBODIMENTS

The detection method and detection kit according to the present invention will now be described.

It is noted here that the term "lectin" used herein refers to a protein which specifically recognizes a particular sugar chain and binds thereto. The term "antigen" used herein means a molecule which comprises a sugar chain recognized by a lectin and can thus be recognized by and bound with the lectin, and this term encompasses proteins (sugar chain proteins), lipids (sugar chain lipids) and the like. The term "detection method" used herein naturally encompasses not only qualitative measurement methods but also quantitative measurement methods (quantitative methods).

<<Lectin, Hydrolase Etc., Used in the Present Invention>>

In the method of the present invention, a lectin, a label, a hydrolase, an antigen-binding molecule and a sample containing an antigen to be detected (analyte) are used. In addition, a support for immobilization of the antigen-binding molecule may also be used. These elements will now each be described in detail.

<Lectin>

As the lectin used in the method of the present invention, a lectin that binds to plural kinds of sugar chains including a particular sugar chain of the antigen to be detected is employed.

Examples of the above-described lectin include lectins belonging to various molecule families obtained from, for example, animals, plants, fungi, bacteria and viruses, that is, ricin B chain-related "R-type lectins" that are found throughout the biological world including bacteria; calcium-requiring "C-type lectins" including many representative lectins such as "calnexin/calreticulin" that is generally present in eukaryotes and participates in folding of glycoproteins, and "selectin" and "collectin" that are widely present in multicellular animals; "galectin" that is widely distributed in the animal kingdom and shows specificity to galactose; "leguminous lectins" that form a large family in Leguminosae plants, and "L-type lectins" that have structural similarity thereto and are involved in intracellular transport in animals; mannose 6-phosphate-binding "P-type lectins" that are involved in intracellular transport of lysosomal enzymes; "annexin" binding to an acidic sugar chain such as glycosaminoglycan; and "I-type lectins" that belong to an immunoglobulin superfamily and include "siglecs".

Examples of other lectins include ACA (*Amaranthus caudates* lectin), BPL (*Bauhinia purpurea* lectin), ConA (*Canavalia ensiformis* lectin), DBA (*Horsegram lectin*), DSA (*Datura stramonium* lectin), ECA (*Erythrina cristagalli* lectin), EEL (Spindle Tree lectin), GNA (*Galanthus nivalis* lectin), GSL I (*Griffonia simplicifolia* lectin), GSL II (*Griffonia simplicifolia* lectin), HHL (*Hippeastrum hybrid* lectin), jacalin (*Artocarpus integrifolia* lectin), LBA (Lima bean lectin), LCA (*Lens culinaris* lectin), LEL (*Lycopersicon esculentum* lectin), LTL (*Lotus tetragonolobus* lectin), MPA (*Maclura pomifera* lectin) NPA (*Narcissus pseudonarcissus* lectin), PHA-E (*Phaseolus Vulgaris* lectin), PHA-L (*Phaseolus Vulgaris* lectin), PNA (*Arachis hypogaea* lectin), PSA (*Pisumsativum* lectin) PTL-I (*Psophocarpus tetragonolobus* lectin), PTL-II (*Psophocarpus tetragonolobus* lectin), PWM (pokeweed lectin), RCA120 (*Ricinus communis* lectin), SBA (soybean lectin) SJA (*Sophora japonica* lectin), SNA (*Sambucus nigra* lectin), SSA (*Sambucus sieboldiana* lectin), STL (*Solanum tuberosum* lectin), TJA-I (*Trichosanthes japonica* lectin), TJA-II (*Trichosanthes japonica* lectin), UDA (Common Stinging Nettle lectin), UEA I (*Ulex europaeus* lectin), VFA (*Vicia faba* lectin), VVA (*Vicia villosa* lectin), WFA (*Wisteria floribunda* lectin) and WGA (wheat germ lectin).

<Label>

In the method of the present invention, a label is used for detection of the above-described lectin bound to an antigen having a particular sugar chain. The label is bound to the lectin and used as a labeled lectin.

As the label, a label known to those of ordinary skill in the art, such as a fluorescent dye, an enzyme, a coenzyme, a chemiluminescent substance or a radioactive substance, can be employed.

Examples of the fluorescent dye include organic fluorescent dyes such as fluorescent dyes of fluorescein family (manufactured by Integrated DNA Technologies, Inc.), fluorescent dyes of polyhalofluorescein family (manufactured by Applied Biosystems Japan, Ltd.), fluorescent dyes of hexachlorofluorescein family (manufactured by Applied Biosystems Japan, Ltd.), fluorescent dyes of coumarin family (manufactured by Invitrogen Corp.), fluorescent dyes of rhodamine family (manufactured by GE Healthcare Bio-Sciences Corp.), fluorescent dyes of cyanine family, fluorescent dyes of indodicarbocyanine family, fluorescent dyes of oxazine family, fluorescent dyes of thiazine family, fluorescent dyes of squaraine family, fluorescent dyes of chelated lanthanide family, fluorescent dyes of BODIPY (registered trademark) family (manufactured by Invitrogen Corp.), fluorescent dyes of naphthalene sulfonate family, fluorescent dyes of pyrene family, fluorescent dyes of triphenylmethane family, and Alexa Fluor (registered trademark) dye series (manufactured by Invitrogen Corp.).

Further, examples of the fluorescent dyes also include fluorescent proteins that are represented by rare earth (e.g., Eu, Tb) complex-based fluorescent dyes (such as ATBTA-$Eu^{3+}$), blue fluorescent proteins (BFP), cyan fluorescent proteins (CFP), green fluorescent proteins (GFP), yellow fluorescent proteins (YFP), red fluorescent proteins (DsRed) and allophycocyanin (APC; LyoFlogen (registered trademark)), and fluorescent particles of latex, silica and the like.

When a sample derived from a blood specimen is analyzed, in order to minimize the effect of light absorption by iron originating from hemocytes in the blood, it is desired to use a fluorescent dye having a maximum fluorescence wavelength in the near-infrared region, such as Cy5 or Alexa Fluor 647.

Examples of the radioactive substance include radio isotopes (such as $^{32}P$, $^{14}C$, $^{125}I$, $^3H$ and $^{131}I$)

<Hydrolase>

As the hydrolase used in the method of the present invention, a glycohydrolase that is capable of cleaving at least one kind of sugar chain to which the above-described lectin can bind, the at least one kind of sugar chain excluding the above-described particular sugar chain among the plural kinds of sugar chains, is employed. The hydrolase is not particularly restricted as long as it has the above-described enzyme activity, and preferred examples thereof include glycohydrolases that are classified as E.C.3.2.1 in the enzyme classification of the International Enzyme Committee, more specifically galactosidase, mannosidase and fucosidase.

[Galactosidase]

As galactosidase that can be used in the present invention, there is no particular restriction as long as it is capable of cleaving the $\beta$1-4 and/or $\beta$1-3 bond(s) of galactose. Some of the glycoproteins and glycolipids contained in serum have a galactose residue at a non-reducing terminal. For example, when detecting $\beta$-N-acetylgalactosamine residue with a lectin such as TJA-II, WFA or SBA, such glycoproteins and glycolipids generate noise and cause a reduction in the sensitivity; however, the detection sensitivity of N-acetylgalactosamine in serum is improved by cleaving the $\beta$1-4 and/or $\beta$1-3 bond(s) of galactose. Galactose has bonds such as $\alpha$1-3, $\beta$1-3 and $\beta$1-4; however, the galactosidase that can be used in the present invention may cleave only the $\beta$1-4 bond or some of the bonds including $\beta$1-4.

Mammals also have galactosidase, and the studies of galactosidases derived from plants, bacteria and protozoan pathogens are in progress. As galactosidase, those which are derived from *Bacteroides fragilis, Xanthomonas manihotis* and HCV are known. Thereamong, one example of galactosidase capable of cleaving the $\beta$1-4 bond of galactose is galactosidase derived from *Bacteroides fragilis*.

[Mannosidase]

As mannosidase that can be used in the present invention, there is no particular restriction as long as it is capable of cleaving the $\alpha$1-2, $\alpha$1-3 and/or $\beta$1-6 bond(s) of mannose. Mannosidase is present in mammals as well, and the studies of mannosidase derived from plants, bacteria and yeast are in progress. As mannosidase, those which are derived from

*Canavalia ensiformis, Xanthomonas manihotis* and African land snail (*Achatina fulica*) are known.

[Fucosidase]

As fucosidase that can be used in the present invention, there is no particular restriction as long as it is capable of cleaving the α1-6 bond of fucose. Fucosidase is widely present in animals including mammals, plants, bacteria, yeast and the like and, for example, fucosidases derived from almond, bovine kidney, *Elizabethkingia miricola* and *Xanthomonas manihotis* are known.

<Antigen-Binding Molecule (Ligand)

The antigen-binding molecule of the present invention (hereinafter, also referred to as "ligand") is not particularly restricted as long as it specifically recognizes and binds to an antigen to be detected (analyte) and does not prevent a lectin from recognizing a sugar chain. For example, an antibody, an aptamer or a synthetic peptide can be used. Thereamong, in the present invention, an antibody is preferably used.

In the present invention, the term "antibody" is used with a meaning that includes not only a complete antibody but also an arbitrary antibody fragment or derivative, encompassing complete antibodies as well as a variety of antibodies such as Fabs, Fab'$_2$s, CDRs, humanized antibodies, polyfunctional antibodies and single-chain antibodies (ScFv).

<Antigen to be Detected (Analyte)>

The antigen to be detected (hereinafter, also referred to as "analyte") may be any molecule or molecular fragment as long as it has a particular sugar chain recognized by a lectin and an antigen-binding molecule can specifically recognize and bind thereto.

Examples of such "molecule" or "molecular fragment" include nucleic acids (such as single-stranded or double-stranded DNAs, RNAs, polynucleotides, oligonucleotides and PNAs (peptide nucleic acids), as well as nucleosides, nucleotides and modified molecules thereof; proteins (such as polypeptides and oligopeptides); amino acids (including modified amino acids); saccharides (such as oligosaccharides, polysaccharides and sugar chains); lipids; and modified molecules and complexes of these molecules. Thereamong, as the analyte, proteins (glycoproteins) and lipids (glycolipids) are preferred and proteins (glycoproteins) are more preferred.

Examples of the proteins include tumor antigens/tumor markers, signal transducers and hormones. More specifically, preferred examples of the proteins include tumor antigens/tumor markers such as PSAs, AFPs and CEAs.

<Sample Containing Antigen to be Detected (Analyte)

The test sample used in the detection method of the present invention is a sample containing the above-described antigen to be detected (analyte) In the analyte-containing sample, in addition to a sample that actually contains the analyte, a sample that potentially contains the analyte is also included. Examples of such analyte-containing sample include biological samples and samples derived from living bodies that contain the analyte; and biological samples and samples derived from living bodies that potentially contain the analyte. Examples of such biological samples and samples derived from living bodies include blood, serum, plasma, urine, spinal fluid, saliva, cells, tissues, organs, and preparations thereof (such as biopsy specimens). The test sample used in the detection method of the present invention is preferably blood, serum or plasma.

The above-described liquid samples such as blood, serum, plasma, urine, spinal fluid and saliva can be diluted with an appropriate buffer prior to use. Further, the solid samples such as cells, tissues and organs can be homogenized with an appropriate buffer to about 2 to 10 times based on volume and the resulting suspension or supernatant thereof can be used as is or after further dilution.

<Combination of Antigen to be Detected, Lectin and Hydrolase>

Table 1 shows specific examples of combinations of an antigen having a particular sugar chain (antigen to be detected), a lectin that binds to plural kinds of sugar chains including the particular sugar chain, and a glycohydrolase that is capable of cleaving at least one kind of sugar chain to which the above-described lectin can bind, the at least one kind of sugar chain excluding the above-described particular sugar chain among the plural kinds of sugar chains.

In addition to those combinations shown in Table 1, taking into consideration the antigen to be detected such as a tumor antigen or tumor marker, glycoproteins and glycolipids other than the antigen to be detected that are likely to be contained in a sample along with the antigen as well as the types of sugar chains contained in the antigen, glycoproteins and glycolipids, a lectin which readily binds to a sugar chain of the antigen and a glycohydrolase which cleaves a sugar chain(s) of glycoproteins and glycolipids to which the lectin may also bind at the same time can be appropriately selected and used in a combination.

It is noted here that, when an antibody is used as the antigen-binding molecule, it is appropriate to use an antigen-specific antibody as the antibody. For example, when human PSA is the antigen, an anti-human PSA antibody may be used.

TABLE 1

| Antigen | Lectin | Glycohydrolase |
|---|---|---|
| Prostate-specific antigen (PSA) | *Wisteria floribunda* lectin (WFA) | galactosidase |
| Prostate-specific antigen (PSA) | Soybean lectin (SBA) | galactosidase |
| Prostate-specific antigen (PSA) | *Trichosanthes japonica* lectin (TJA-II) | fucosidase |
| α-fetoprotein (AFP) | *Lens culinaris* lectin (LCA) | Mannosidase |
| Carcinoembryonic antigen (CEA) | *Trichosanthes japonica* lectin (TJA-I) | galactosidase |
| α-fetoprotein (AFP) | *Aleuria aurantia* lectin (AAL) | fucosidase |
| CA125 antigen (CA125) | Wheat germ lectin (WGA) | N-acetylglucosaminidase |
| Thyroglobulin | *Canavalia ensiformis* lectin (ConA) | glucosidase |

<Support>

In the detection method of the present invention, a support can be used for immobilizing an antigen-binding molecule thereon. Examples of the support include insoluble polysaccharides such as agarose and cellulose; synthetic resins such as silicon resins, polystyrene resins, polyacrylamide resins, nylon resins and polycarbonate resins; and insoluble supports made of glass or the like. These supports are used in the form of, for example, beads (mainly spherical) or a plate (mainly planar). As the beads, for example, magnetic beads or resin beads that are filled in a column or the like can be used. In the case of a plate, for example, a multi-well plate (such as a 96 multi-well plate) or a biosensor chip can be used. Such support is also called "solid-phase material" and a planar support such as a plate is referred to as "substrate".

The antigen-binding molecule and the support can be bound with each other by a commonly used method such as chemical binding or physical adsorption. As the support, any commercially available one can be suitably used.

Here, the binding of the antigen-binding molecule and the support is referred to as "solid-phasing" and the support bound with the antigen-binding molecule is also referred to as "solid-phased support".

<<Detection Method of the Present Invention>>
<Steps Included in Detection Method>

The detection method of the present invention is a method of detecting an antigen having a particular sugar chain in a sample with a lectin that binds to plural kinds of sugar chains including the particular sugar chain, and the detection method comprises the following steps.

(1) a first step of bringing the above-described lectin into contact with the sample ("the lectin-binding step");

(2) a second step of bringing a glycohydrolase capable of cleaving at least one kind of sugar chain to which the lectin can bind into contact with the sample, the at least one kind of sugar chain excluding the particular sugar chain among the plural kinds of sugar chains ("the sugar chain-cleaving step"); and (4) a fourth step of detecting the antigen bound with the lectin, which is carried out after the first and second steps ("the detection step").

The detection method of the present invention may further comprise the following step:

(3) a third step of bringing the sample into contact with a support on which a molecule binding to the above-described antigen is immobilized, the third step being carried out before the above-described fourth step ("the antigen-capturing step").

<Order of Carrying Out Steps (Step Order)>

In the method of the present invention, the above-described steps can be carried out in any order as long as the detection step (the fourth step) is carried out at the end. Further, the lectin-binding step (the first step) and the sugar chain-cleaving step (the second step) can be carried out simultaneously as well, Specifically, preferred examples of the order of carrying out the steps include the below-described orders. It is noted here that the expression "the first step+the second step" indicates that the first and second steps are carried out simultaneously and the symbol "→" means that the step shown in the left of the symbol is carried out before the step shown in the right. For instance, "(the first step+the second step)→the third step→the fourth step" indicates that the first and second steps are carried out simultaneously and the third step is then carried out, followed by the fourth step.

(Step Orders of the Present Invention)

(1) (the first step+the second step)→the fourth step
(2) the first step→the second step→the fourth step
(3) the second step→the first step→the fourth step
(4) (the first step+the second step)→the third step→the fourth step
(5) the first step→the second step the third step→the fourth step
(6) the second step→the first step→the third step→the fourth step
(7) the first step→the third step→the second step→the fourth step
(8) the second step→the third step→the first step→the fourth step
(9) the third step→(the first step+the second step)→the fourth step
(10) the third step→the first step→the second step→the fourth step
(11) the third step→the second step→the first step→the fourth step FIGS. 2 to 4 are conceptual diagrams showing some of these step orders. FIGS. 2 to 4 are conceptual diagrams corresponding to the above-described step orders of (4), (8) and (11), respectively. In these figures, a lectin that binds to plural kinds of sugar chains including a particular sugar chain recognizes both a particular sugar chain (46c) and a sugar chain (46d) which excludes the particular sugar chain and to which the lectin can bind. For example, in a case where WFA lectin is used for a PSA antigen, the particular sugar chain (46c) corresponds to N-acetyl-D-galactosamine (GalNAc) and the sugar chain (46d), which excludes the particular sugar chain and to which the lectin can bind, corresponds to galactose (Gal).

One example of a method of carrying out the steps of the present invention without the third step is a method in which an antibody labeled with a donor fluorophore of FRET (Fluorescence Resonance Energy Transfer) reagent is used as an antigen-binding molecule and an acceptor fluorophore of FRET reagent is used as a lectin-labeling label. In this case, glycoproteins and glycolipids that are not the detection target non-specifically bind to the antigen-binding molecule (antibody) to cause an increase in background. Thus, the increased background can be reduced by the detection method of the present invention which comprises the first, second and fourth steps, thereby the effects of the present invention can be attained.

From the standpoint of increasing the detection sensitivity, it is preferred that the method of the present invention include the third step (the antigen-capturing step).

The orders of carrying out the second step (the sugar chain-cleaving step) in the whole steps are largely classified into (A) cases where the second step is carried out on a support after the third step (the antigen-capturing step) and (B) other cases (where the sugar chain-cleaving step is carried out before the antigen-capturing step or the antigen-capturing step is not carried out).

In the cases of (A), a sample is first brought into contact with a support on which an antigen-binding molecule (such as an antibody) is solid-phased (immobilized). On the support with which the sample is brought into contact, serum glycoproteins and glycolipids are non-specifically adsorbed. By adding thereto an enzyme capable of cleaving sugar chains other than a particular sugar chain, the sugar chains other than the particular sugar chain can be cleaved and removed from the glycoproteins and glycolipids that are non-specifically bound to the support and antigen-binding molecule. This inhibits an increase in the background caused by an addition of a lectin.

In the cases of (B), with or without diluting a sample potentially containing an analyte with an appropriate buffer, an enzyme capable of cleaving sugar chains other than a specific sugar chain is added to the sample. By this, sugar chains that are noise components can be removed from other proteins contained in the antigen-containing sample and the specificity and sensitivity are improved.

As compared to the cases of (B) where the enzyme treatment is performed in a large amount of contaminants, the cases of (A) where only those contaminants adsorbing to the support and antigen-binding molecule are treated show superior noise-removing effect and are thus more preferred.

Further, it is preferred that the second step (the sugar chain-cleaving step) be carried out before the first step (the lectin-binding step). This is because, when a lectin is bound and its sugar chain is then cleaved, the cleaving efficiency is reduced due to steric hindrance and the like and the background is thus increased.

The method of the present invention can also be carried out in combination with a conventional background suppression method and such combination is expected to provide superior background-suppressing effect.

<Details of Each Step>

The steps will now each be described in detail.

[1. First Step (Lectin-Binding Step)]

The first step is where a lectin that binds to plural kinds of sugar chains including a particular sugar chain is allowed to bind to an antigen having the particular sugar chain. The amount, concentration in a reaction solution, reaction time and reaction conditions of the lectin used in this step may be adjusted as appropriate in accordance with the type of the lectin.

[2. Second Step (Sugar Chain-Cleaving Step)]

The second step is where a glycohydrolase capable of cleaving at least one kind of sugar chain to which the above-described lectin can bind into contact with the sample, the at least one kind of sugar chain excluding the above-described particular sugar chain among the above-described plural kinds of sugar chains, so as to cleave the at least one sugar chain excluding the particular sugar chain. The amount, concentration in a reaction solution, reaction time and reaction conditions of the glycohydrolase used in this step may be adjusted as appropriate in accordance with the type of the glycohydrolase.

For example, in cases where galactosidase derived from *Bacteroides fragilis* is used, the β1-4 bond of galactose in serum glycoproteins and glycolipids can be cleaved using the galactosidase in an amount of 2 to 1,000 mU, preferably 20 to 100 mU.

The galactosidase treatment (reaction) time is normally 10 minutes to 24 hours, preferably 30 minutes to 1 hour. The reaction temperature is preferably 25° C. to 40° C.

Further, for example, in cases where mannosidase derived from *Canavalia ensiformis* is used, the bonds of mannose in serum glycoproteins and glycolipids can be cleaved using the mannosidase in an amount of 2 to 1,000 mU, preferably 20 to 100 mU.

The mannosidase treatment (reaction) time is normally 10 minutes to 24 hours, preferably 30 minutes to 1 hour. The reaction temperature is preferably 25° C. to 40° C.

[3. Third Step (Antigen-Capturing Step)]

The third step is where the antigen having the particular sugar chain is allowed to bind to an antigen-binding molecule immobilized on a support (such as a substrate). The reaction conditions such as reaction time and reaction temperature may be adjusted as appropriate in accordance with the antigen and antigen-binding molecule that are used.

[4. Fourth Step (Detection Step)]

The fourth step is where the lectin is detected by measuring a label bound thereto and an antigen to be detected, to which the lectin is bound, is further detected.

(Measuring Method)

The detection method used in the detection step of the present invention is not particularly restricted as long as it is capable of measuring the above-described label, and the detection can be performed by a method that is suitable for each labeling substance and known to those of ordinary skill in the art. For example, in cases where a lectin labeled with a radioactive substance is to be detected, the detection can be performed by liquid scintillation or a RIA method. In cases where a lectin labeled with a fluorescent dye is to be detected, the detection can be performed using a luminometer, a SPFS measurement apparatus or the like. In cases where a lectin labeled with an enzyme is to be detected, the detection can be performed by adding a substrate corresponding to the labeling enzyme and then measuring a chemical change of the substrate caused by the enzyme, such as color development, fluorescence or chemiluminescence.

[Surface Plasmon-field Enhanced Fluorescence Spectroscopy: SPFS) Method]

As a measuring method to be used in the detection, method of the present invention, SPFS is preferred. SPFS is a method which utilizes a phenomenon that an evanescent wave transmitting through a metal thin film is enhanced by several tens to several hundreds of times due to resonance with surface plasmon when the metal thin film formed on a dielectric member is irradiated with an excitation light at an angle that causes attenuated total reflection (ATR), thereby efficiently exciting a fluorescent material labeling an analyte (analysis subject) captured in the vicinity of the metal thin film so as to measure its fluorescence signal. Such SPFS is extremely sensitivity as compared to ordinary fluorescent labeling methods and the like; therefore, it is capable of quantifying an analyte even when the analyte is present in a sample only in a trace amount.

<Measuring Member for SPFS>

A measuring member for SPFS generally has a constitution in which a sensor chip, on which a place (measurement region) where a sandwich-type immunocomplex is formed for fluorescence measurement by SPFS is provided, and a member for constructing a flow path or well, which member is capable of retaining a variety of solutions used in the formation of a sandwich-type immunocomplex and the like (e.g., analyte-containing sample, labeling ligand solution and other reaction reagents) on the measurement region, are laminated.

The sensor chip basically comprises: a transparent support for introducing an excitation light to the backside of a metal thin film; a metal thin film for generating surface plasmon resonance, which is formed on the transparent support; and a reaction layer for capturing an analyte on the sensor surface, which is formed on the metal thin film. As required, the sensor chip may further comprise a spacer layer for inhibiting metal extinction of fluorescence caused by excessive proximity of fluorescent material to the metal thin film, which spacer layer is formed between the metal thin film and the reaction layer.

The part where the reaction layer is formed corresponds to the measurement region. The measurement region may be provided by forming the reaction layer on the entire bottom surface of a flow path or well or by forming the reaction layer only on a portion of the bottom surface (with a desired pattern as required). The area of the measurement region can be adjusted, taking into consideration the irradiation area of the excitation light that is generally irradiated as a laser beam. For example, when the spot diameter of the excitation light is 1 mmφ or so, the above-described assay area is normally designed to have an area of at least several mm-square.

In cases where a SPFS system of "flow-path type" in which various solutions are transferred through a closed flow path is employed, a "flow cell" having holes for forming a flow path is mounted on the sensor chip and, as required, a "top plate" having a solution inlet and a solution outlet at the positions corresponding to the holes of the above-described flow cell is further mounted on the flow cell. These components are tightly adhered with each other and immobilized to construct a measuring member. The sensor chip surface at the positions corresponding to the holes of the above-described flow cell constitutes the bottom surface of the flow path and the measurement region is formed thereon. In the case of a flow path-type system, for example, by using a liquid transfer means comprising a pump or tube, various liquids can be introduced to the flow path via the solution inlet and discharged from the solution outlet. As required, the liquid transfer can also be performed in a reciprocating manner or circulating manner. The conditions such as liquid transfer rate and liquid transfer (circulation) time can be adjusted as appropriate, taking into consideration the sample amount, the analyte concentration in the sample, the size of the flow path or well, the mode of the reaction layer (e.g., the density of immobilized ligand), the pump performance and the like.

Meanwhile, in cases where a SPFS system of "well type" in which various solutions are retained in a space larger than the above-described flow path is employed, a "well member" having a through-hole for forming a well is mounted and immobilized on the sensor chip to construct a measuring member. In the case of a well-type system, various liquids can be added to and removed from the well using, for example, a pipette-form member.

The above-described flow cell can be made of, for example, a sheet-form polydimethylsiloxane (PDMS). The above-described top plate is produced from a transparent material so that fluorescence emitted from the measurement region can be measured, and the top plate can be made of, for example, a plate-form polymethyl methacrylate (PMMA). Alternatively, the flow cell and the top plate can be made of plastic having a desired shape obtained by molding or photolithography.

The means for tightly adhering and immobilizing the flow cell or well member on the sensor chip is not particularly restricted and, generally, pressure can be physically applied thereto from both the top and the bottom. If necessary, an adhesive having the same refractive index as the transparent support, a matching oil, a transparent adhesive sheet or the like may also be used.

<SPFS Measurement Apparatus>

The measurement method according to the present invention can be carried out using an ordinary SPFS measurement apparatus. Basically, the SPFS measurement apparatus has a detachable measuring member for SPFS and comprises, for example, a light source for irradiating an excitation light (preferably a laser beam) that has a wavelength appropriate for the fluorescent material used; a prism for allowing the excitation light to enter the backside of a metal thin film of a sensor chip at a prescribed angle (when a sensor chip having a planar substrate-form transparent support is used); a light receiver which receives light reflected by the metal thin film and measures the intensity thereof; a lens for condensing fluorescence emitted from the fluorescent material; a detector for measuring the intensity of the fluorescence; and various filters that allow only light having a prescribed wavelength from the excitation light and fluorescence to transmit therethrough and cut other lights.

For more concrete embodiments, reference can be made to various documents such as Japanese Laid-open Patent Application (Kokai) No. 2010-145272, Japanese Laid-open Patent Application (Kokai) No. 2011-80935, Japanese Laid-open Patent Application (Kokai) No. 2008-102117 and Japanese Patent No. 3562912.

A more detailed example of the constitution of SPFS measurement apparatus will now be described.

1. Constitution of Quantitative Measurement Apparatus

FIG. 5 is a drawing which schematically shows the outline of a quantitative measurement apparatus for illustrating the method of quantitatively measuring an analyte according to the present invention, and FIG. 6 is a partially enlarged view of the quantitative measurement apparatus shown in FIG. 5.

As shown in FIGS. 5 and 6, a quantitative measurement apparatus 10 of the present invention comprises: a prism-shaped dielectric member 12 whose vertical cross-sectional shape is substantially trapezoidal; and a sensor chip 16 having a metal film 14 formed on a horizontal upper surface 12a of the dielectric member 12, and the sensor chip 16 is mounted to a sensor chip mounting section 18 of the quantitative measurement apparatus 10.

Also, as shown in FIG. 5, a light source 20 is arranged on the side of a lower side surface 12b of the dielectric member 12. From this light source 20, an incoming light 22 enters the side surface 12b of the dielectric member 12 from the lower outside of the dielectric member 12 and is irradiated via the dielectric member 12 toward the metal film 14 formed on the upper surface 12a of the dielectric member 12.

Further, between the light source 20 and the dielectric member 12, a polarizing filter, which is used for P-polarizing a laser beam emitted from the light source 20 so as to allow surface plasmon to be efficiently generated on the metal film 14, may also be arranged.

As shown in FIG. 5, on the side of the other side surface 12c and inferiorly to the dielectric member 12, a light-receiving means 26, which receives metal film-reflected light 24 which is the incoming light 22 reflected by the metal film 14, is provided.

The light source 20 comprises an incidence angle-adjusting means (not shown), which is capable of appropriately altering an incidence angle $\alpha 1$ of the incoming light 22 emitted from the light source 20 with respect to the metal film 14. Meanwhile, the light-receiving means 26 also comprises a movable means not shown in the figure and is constituted in such a manner to ensure reception of the metal film-reflected light 24 in synchronization with the light source 20 even when the reflection angle of the metal film-reflected light 24 is altered.

An SPR-measuring section 28 of the quantitative measurement apparatus 10 according to the present invention, which performs SPR measurement, is constituted by the sensor chip 16, the light source 20 and the light-receiving means 26.

Further, above the sensor chip 16, a light-detecting means 32, which is used for receiving fluorescence 30 emitted by excitation of the below-described fluorescent substance, is provided.

Between the sensor chip 16 and the light-detecting means 32, for example, a cut filter or a condenser lens may also be arranged.

An SPFS measurement section 34 of the quantitative measurement apparatus 10 according to the present invention, which performs SPFS measurement, is constituted by the sensor chip 16, the light source 20 and the light-detecting means 32.

Further, the light-receiving means 26 and the light-detecting means 32 are each connected to a quantitative calculation means 40 and configured in such a manner that the amount of the metal film-reflected light 24 received by the light-receiving means 26 and the amount of the fluorescence 30 received by the light-detecting means 32 are transmitted to the quantitative calculation means 40.

Moreover, in the sensor chip 16 of this example, a flow path 36 is formed on upper surface 14a of the metal film 14. On apart of this flow path 36, a sensor section 38, in which a molecule (ligand) that specifically binds to an antigen to be detected (analyte) is solid-phased, is arranged.

<<Detection Kit>>

The detection kit of the present invention is used in the above-described detection method of the present invention. The detection kit of the present invention comprises:

(1) a reagent which comprises a lectin that binds to plural kinds of sugar chains including a particular sugar chain;

(2) a reagent which comprises a glycohydrolase capable of cleaving at least one kind of sugar chain to which the above-described lectin can bind, the at least one kind of sugar chain excluding the above-described particular sugar chain among the plural kinds of sugar chains; and (3) a reagent which comprises a molecule that binds to an antigen having the above-described particular sugar chain.

The detection kit of the present invention may further comprise:

(4) a user manual in which the detection method of the present invention is described as instruction; and/or (5) a lectin-labeled reagent.

The (4) user manual included in the kit describes any one of the detection methods according to the present invention as instruction for carrying out the method of the present invention. As for a specific embodiment of the user manual, the user manual may assume any embodiment as long as it can properly convey the above-described information. For example, the user manual may be printed on a piece of paper, the package of the kit, a label of the kit constituents or the like, or recorded in a medium readable by a computer, such as a diskette or a CD.

The (5) lectin-labeled reagent included in the kit is a reagent to be used for labeling a lectin and usually contains a label and a reagent which allows the lectin and label to bind with each other.

<<Application Examples>>

The method of the present invention can be used in diagnosis of diseases. For example, when, the antigen to be detected (analyte) is a PSA, prostate adenocarcinoma can be diagnosed based on the amount of PSA in a biological sample derived from a patient that is quantified by the detection method of the present invention.

In addition, hepatocellular carcinoma can be diagnosed when the analyte is an AFP, and cancers mainly associated with gastrointestinal tract can be diagnosed when the analyte is a CEA.

EXAMPLES

The present invention will now be described in detail by way of examples thereof; however, the present invention is not restricted thereto.

(Constitution of Quantitative Measurement Apparatus)

In the following Examples, as a measurement apparatus, the above-described SPFS measurement apparatus which was personally produced by the present inventors was employed. This SPFS measurement apparatus has the same constitution as the above-described quantitative measurement apparatus 10.

In the above-described constitution, a laser diode (LD) capable of irradiating light having a wavelength of 635 nm was used as the light source 20 and a light attenuation filter (neutral density filter) was arranged as an optical filter between the light source 20 and the dielectric member 12 so as to be able to adjust the photon amount.

Further, as the dielectric member 12, a 60° prism manufactured by Sigma Koki Co., Ltd. was used, and the sensor chip 16 was constructed by immobilizing the below-described plasmon excitation sensor on the upper part of this dielectric member 12.

Moreover, on the upper part of the sensor chip 16, an objective lens was provided as a condenser lens, and a photomultiplier tube (PMT) was used as the light-detecting means 32.

(Preparation of Plasmon Excitation Sensor)

A glass-made transparent planar substrate having a refractive index of 1.72 and a thickness of 1 mm (S-LAL 10, manufactured by Ohara Inc.) was cleaned with plasma and a chromium thin film was formed on one side of this substrate by a sputtering method. Then, on the surface of the thus formed chromium thin film, a gold thin film was further formed by a sputtering method. The chromium thin film had a thickness of 1 to 3 nm and the gold thin film had a thickness of 44 to 52 nm.

The substrate on which the gold thin film was formed in this manner was immersed in an ethanol solution containing 1 mM of 10-carboxy-1-decanethiol for at least 24 hours to form a SAM film on the surface of the gold thin film. The substrate was then removed from the solution and washed with ethanol and isopropanol, followed by drying using an air gun.

A polydimethylsiloxane (PDMS) sheet, which had a groove of 0.5 mm in height serving as a flow path as well as a through-hole at both ends of the groove, was disposed on the substrate with the groove facing the SAM film such that the surface of the SAM film was arranged inside the flow path. The PDMS sheet outside the flow path was press-adhered from above, and the PDMS sheet (flow path 36) was immobilized with the plasmon excitation sensor.

Solid-phasing of Antibody

Preparation Example 1

[Anti-PSA Antibody-Solid Phased SAM Film (Substrate)]

In the external flow path to which the plasmon excitation sensor was connected as described above, ultrapure water and then phosphate buffered saline (PBS) were circulated for 10 minutes and 20 minutes, respectively, using a peristaltic pump at a room temperature (25° C.) and a flow rate of 500 uL/min, thereby equilibrating the surface of the plasmon excitation sensor.

Subsequently, after transferring and circulating 5 mL of a phosphate buffered saline (PBS) containing 50 mM of N-hydroxysuccinic acid imide (NHS) and 100 mM of water-soluble carbodiimide (WSC) for 20 minutes, 2.5 mL of an anti-PSA monoclonal antibody solution (No. 79, 2.5 mg/mL; manufactured by Mikuri Immunolaboratory, Ltd.) was circulated for 30 minutes to solid-phase the antibody on the SAM film, thereby preparing an anti-PSA antibody-solid phased SAM film.

It is noted here that a non-specific adsorption-inhibiting treatment was performed in the flow path by circulating therein a phosphate buffered saline (PBS) containing 1 wt % of bovine serum albumin (BSA) for 30 minutes.

As shown in FIG. 7, the sensor section 38 before transfer of various pooled serum samples thereto is in a condition where the above-described antibody (ligand 44) is formed.

Preparation Example 2

[Anti-AFP Antibody-Solid Phased SAM Film (Substrate)]

An anti-AFP antibody-solid phased SAM film was prepared in the same manner as in Preparation Example 1, except that an anti-AFP monoclonal antibody (1D5, 2.5 mg/mL; manufactured by Japan Clinical Laboratories, Inc.) was used in place of the anti-PSA antibody.

Preparation of Labeled Lectins

Production Example 1

[Fluorescently-Labeled WFA Lectin]

A fluorescently-labeled WFA lectin was produced using a fluorescent substance labeling kit, "Alexa Fluor (registered trademark) 647 Protein Labeling Kit" (manufactured by Invitrogen Corp.). Then, 100 μg equivalent of a WFA lectin (L-1350, manufactured by Vector Laboratories, Inc.), 0.1M sodium bicarbonate and Alexa Fluor 647 reactive dye were mixed and allowed to react at room temperature for 1 hour. Subsequently, the resultant was subjected to gel filtration chromatography and ultrafiltration, thereby removing Alexa Fluor 647 reactive dye that was not utilized in labeling to obtain a fluorescently-labeled WFA lectin. Thereafter, the absorbance was measured to determine the concentration of the labeled lectin.

Production Example 2

[Fluorescently-Labeled LCA Lectin]

A fluorescently-labeled LCA lectin was produced using a fluorescent substance labeling kit. The fluorescently-labeled LCA lectin was obtained in the same manner as in Production Example 1, except that an LCA lectin (L-1040, manufactured by Vector Laboratories, Inc.) was used as the lectin.
<Measurement of PSA in Serum Sample>

Example 1

(Measurement of PSA in Serum Sample (1))

Each sample was subjected to an enzyme treatment with galactosidase and then brought into contact with the thus obtained fluorescently-labeled WFA lectin (Production Example 1). Subsequently, the resulting sample was allowed to react with the anti-PSA antibody-solid phased substrate (Preparation Example 1). More particularly, measurement of PSA in each sample was carried out as follows.

A total of 10 samples, consisting of 5 kinds of PSA-free pooled human sera (normal human pooled sera, manufactured by Kohjin Bio Co., Ltd.) and 5 serum samples in which a LNCaP (human prostate adenocarcinomal cell line) culture supernatant was added to the respective PSA-free pooled sera at a PSA concentration of 50 pg/mL, were prepared and then 2-fold diluted with PBS to obtain measurement samples. As the above-described PSA-free pooled human sera, normal human pooled sera were purchased from Kohjin Bio Co., Ltd. and confirmed by ELISA to have a PSA concentration of not higher than 0.01 ng/mL.

To 0.1 mL of each measurement sample, galactosidase derived from Bacteroides fragilis was added to a final concentration of 50 mU, and the resultant was allowed to react at 37° C. for 1 hour. Then, as a fluorescently-labeled probe 48, 0.1 mL of a solution of WFA lectin labeled with Alexa Fluor 647 (in which the Alexa Fluor 647-labeled WFA lectin was dissolved in phosphate buffered saline (PBS) at a concentration of 1 μg/mL) was added, and the resultant was allowed to react at room temperature for 1 hour. The resulting measurement sample, which was thus subjected to the galactosidase treatment and lectin reaction, was added in an amount of 0.1 mL to the flow path and circulated therein for 20 minutes at a flow rate of 200 μL/min. Subsequently, TBS containing 0.05 wt % of Tween 20 (TBS-T) was introduced thereto to perform 5-minute washing. Thereafter, SPFS measurement was carried out using the quantitative measurement apparatus. Measurement samples were also prepared without the galactosidase treatment step and subjected to SPFS measurement in the same manner. FIG. 8 is an enlarged view which schematically shows the sensor section after the transfer of the labeled lectin thereto.

The results of preparing and measuring the measurement samples by the above-described methods are shown in Table 2 below. The results shown in Table 2 are actually measured values. The signal values of the PSA-added sera denote those of "PSA-originated signal value+background".

TABLE 2

Relationship between Enzyme Treatment in Solution and Background (PSA)

| | Galactosidase (−) | Galactosidase (+) |
|---|---|---|
| Pooled serum 1 (PSA-free) | 57,600 | 30,200 |
| Pooled serum 2 (PSA-free) | 55,400 | 38,900 |
| Pooled serum 3 (PSA-free) | 58,000 | 43,000 |
| Pooled serum 4 (PSA-free) | 52,000 | 32,300 |
| Pooled serum 5 (PSA-free) | 49,900 | 35,600 |
| Pooled serum 1 (with addition of LNCaP-derived PSA at 50 pg/mL) | 107,600 | 80,300 |
| Pooled serum 2 (with addition of LNCaP-derived PSA at 50 pg/mL) | 110,400 | 92,300 |
| Pooled serum 3 (with addition of LNCaP-derived PSA at 50 pg/mL) | 110,200 | 82,900 |
| Pooled serum 4 (with addition of LNCaP-derived PSA at 50 pg/mL) | 110,200 | 88,300 |
| Pooled serum 5 (with addition of LNCaP-derived PSA at 50 pg/mL) | 110,800 | 83,600 |

It was confirmed that, in the measurement samples treated with galactosidase, the values of the respective PSA-free pooled sera (background) were reduced to a level of about ⅗ as compared to the untreated samples.

In addition, while the average S/N ratio value (signal value of PSA-added serum/signal value of corresponding PSA-free serum) of 5 samples was 2.02 in the untreated samples, it was increased to 2.41 in the galactosidase-treated samples, revealing that the detection sensitivity was increased.

Example 2

(Measurement of PSA in Serum Sample (2))

Each sample was subjected to an enzyme treatment with galactosidase and then allowed to react with the anti-PSA antibody-solid phased substrate (Preparation Example 1). Thereafter, the resulting sample was brought into contact with the fluorescently-labeled WFA lectin (Production Example 1). More particularly, measurement of PSA in each sample was carried out as follows.

A total of 10 samples, consisting of 5 kinds of PSA-free pooled sera and 5 serum samples in which a LNCaP culture supernatant was added to the respective PSA-free pooled sera at a PSA concentration of 50 pg/mL, were prepared and then 2-fold diluted with PBS to obtain measurement samples. To each measurement sample, galactosidase derived from Bacteroides fragilis was added to a final concentration of 50 mU, and the resultant was allowed to react at 37° C. for 1 hour. The thus galactosidase-treated measurement sample was added in an amount of 0.1 mL to the flow path and circulated therein for 20 minutes at a flow rate of 200 μL/min. Subsequently, TBS containing 0.05 wt % of Tween 20 (TBS-T) was introduced thereto to perform 5-minute washing. After the reaction, as the fluorescently-labeled probe 48, 0.1 mL of a solution of WFA lectin labeled with Alexa Fluor 647 (in which the Alexa Fluor 647-labeled WFA lectin was dissolved in phosphate buffered saline (PBS) at a concentration of 1 μg/mL) was added, and the resultant was allowed to flow for 5 minutes at a flow rate of 200 μL/min. Once again, TBS containing 0.05 wt % of Tween 20 (TBS-T) was introduced to perform 5-minute washing. Thereafter, SPFS measurement was carried out using the quantitative measurement apparatus. Measurement samples were also prepared without the galactosidase treatment step and subsequently subjected to SPFS measurement.

The results of measuring the measurement samples by the above-described method are shown in Table 3 below. The results shown in Table 3 are actually measured values. The signal values of the PSA-added sera denote those of "PSA-originated signal value+background".

TABLE 3

Relationship between Enzyme Treatment in Solution and Background (PSA)

|  | Galactosidase (−) | Galactosidase (+) |
|---|---|---|
| Pooled serum 1 (PSA-free) | 32,100 | 10,200 |
| Pooled serum 2 (PSA-free) | 33,400 | 9,900 |
| Pooled serum 3 (PSA-free) | 35,000 | 14,000 |
| Pooled serum 4 (PSA-free) | 32,000 | 12,300 |
| Pooled serum 5 (PSA-free) | 32,500 | 11,300 |
| Pooled serum 1 (with addition of LNCaP-derived PSA at 50 pg/mL) | 84,100 | 60,300 |
| Pooled serum 2 (with addition of LNCaP-derived PSA at 50 pg/mL) | 88,400 | 62,300 |
| Pooled serum 3 (with addition of LNCaP-derived PSA at 50 pg/mL) | 89,300 | 63,900 |
| Pooled serum 4 (with addition of LNCaP-derived PSA at 50 pg/mL) | 90,200 | 68,300 |
| Pooled serum 5 (with addition of LNCaP-derived PSA at 50 pg/mL) | 82,800 | 59,300 |

It was confirmed that, in the measurement samples treated with galactosidase, the signal values of the respective PSA-free pooled sera (background) were reduced to a level of about ⅓ as compared to the untreated samples.

In addition, while the average S/N ratio value (signal value of PSA-added serum/signal value of corresponding PSA-free serum) of 5 samples was 2.64 in the untreated samples, it was increased to 5.51 in the galactosidase-treated samples, revealing that the detection sensitivity was increased.

Example 3

(Measurement of PSA in Serum Sample (3))

Next, a method of performing an enzyme treatment on a substrate will also be described.

After allowing each sample to react with the anti-PSA antibody-solid phased substrate (Preparation Example 1), the resulting sample was subjected to an enzyme treatment with galactosidase and then brought into contact with the fluorescently-labeled WFA lectin (Production Example 1). More particularly, measurement of PSA in each sample was carried out as follows.

A total of 10 samples, consisting of 5 kinds of PSA-free pooled sera and 5 serum samples in which a LNCaP culture supernatant was added to the respective PSA-free pooled sera at a PSA concentration of 50 pg/mL, were prepared and then 2-fold diluted with PBS to obtain measurement samples. The thus obtained 10 pooled serum sample solutions were each added in an amount of 0.1 mL to the flow path and circulated therein for 20 minutes. Subsequently, 0.1 mL of a solution containing 50 mU of galactosidase derived from *Bacteroides fragilis* or PBS(−) was added and the resultant was circulated for 20 minutes. Thereafter, TES containing 0.05 wt % of Tween 20 (TBS-T) was introduced thereto to perform 5-minute washing at a flow rate of 200 μL/min. After the washing, as the fluorescently-labeled probe 48, 0.1 mL of a solution of WFA lectin labeled with Alexa Fluor 647 (in which the Alexa Fluor 647-labeled WFA lectin was dissolved in phosphate buffered saline (PBS) at a concentration of 1 μg/mL) was added, and the resultant was allowed to flow for 5 minutes at a flow rate of 200 μL/min. Then, TBS containing 0.05 wt % of Tween 20 (TBS-T) was again introduced thereto to perform 5-minute washing at a flow rate of 200 μL/min. Finally, SPFS measurement was carried out using the quantitative measurement apparatus. The SPFS measurement was also carried out for samples that were prepared without the galactosidase treatment step.

The results are shown in Table 4. The results shown in Table 4 are actually measured values. The signal values of the PSA-added sera denote those of "PSA-originated signal value+background".

TABLE 4

Relationship between Enzyme Treatment on Substrate and Background (PSA)

|  | Galactosidase (−) | Galactosidase (+) |
|---|---|---|
| Pooled serum 1 (PSA-free) | 22,300 | 4,000 |
| Pooled serum 2 (PSA-free) | 21,400 | 4,500 |
| Pooled serum 3 (PSA-free) | 20,200 | 3,400 |
| Pooled serum 4 (PSA-free) | 18,000 | 4,800 |
| Pooled serum 5 (PSA-free) | 22,200 | 5,200 |
| Pooled serum 1 (with addition of LNCaP-derived PSA at 50 pg/mL) | 67,300 | 58,000 |
| Pooled serum 2 (with addition of LNCaP-derived PSA at 50 pg/mL) | 71,400 | 56,900 |
| Pooled serum 3 (with addition of LNCaP-derived PSA at 50 pg/mL) | 73,200 | 53,400 |
| Pooled serum 4 (with addition of LNCaP-derived PSA at 50 pg/mL) | 76,300 | 57,800 |
| Pooled serum 5 (with addition of LNCaP-derived PSA at 50 pg/mL) | 72,700 | 52,200 |

It was confirmed that, in the measurement samples treated with galactosidase on the substrate, the values of the respective PSA-free pooled sera (background) were reduced to a level of about ¼ as compared to the untreated samples.

In addition, while the average S/N ratio value (signal value of PSA-added serum/signal value of corresponding PSA-free serum) of 5 samples was 3.50 in the untreated samples, it was increased to 12.99 in the galactosidase-treated samples, revealing that the detection sensitivity was increased.

As shown in the above Examples 1 to 3, it was confirmed that non-specific binding signal generated in the measurement system by serum component can be suppressed by cleaving galactose on serum glycoprotein and that the sensitivity for specifically detecting the GalNAc sugar chain structure on PSA is consequently improved.

Moreover, as a result of comparing Examples 2 and 3, it was confirmed that the enzyme treatment exerts superior effect when performed on an antibody-immobilized substrate with a certain level of focus on the treatment subject than when the enzyme is made to act in a solution containing a large amount of serum proteins.

<Measurement of AFP in Serum Sample>

In the above Examples 1 to 3, tests were conducted using PSA as a detection subject; however, a similar test was also performed here using AFP as a detection subject. This test will be described below as Examples 4 to 6. In Examples 4 to 6, a total of 10 samples, consisting of 5 kinds of AFP-free pooled sera used as negative control samples and 5 serum samples used as positive control samples in which μTASWako AFP-L3 Control L (trade name, manufactured by Wako Pure Chemical Industries, Ltd.; L3=20%, AFP concentration=200 ng/mL) was added to the respective AFP-free pooled sera at an AFP concentration of 1.0 ng/mL, were prepared. Here, as the above-described AFP-free pooled human sera, normal human pooled sera were purchased from Kohjin Bio Co., Ltd. and confirmed by ELISA to have an AFP concentration of not higher than 0.01 ng/mL.

Example 4

(Measurement of AFP in Serum Sample (1))

Each sample was subjected to an enzyme treatment with mannosidase and then brought into contact with the fluorescently-labeled LCA lectin (Production Example 2). Subsequently, the resulting sample was allowed to react with the anti-AFP antibody-solid phased substrate (Preparation Example 2).

More particularly, measurement of AFP in each sample was carried out in the same manner as in Example 1, except that: mannosidase derived from *Canavalia ensiformis* (GKX-5010, manufactured by ProZyme, Inc.) was used in place of the galactosidase; the fluorescently-labeled LCA lectin (Production Example 2) was used in place of the fluorescently-labeled WFA lectin (Production Example 1); and the anti-AFP antibody-solid phased substrate (Preparation Example 2) was used in place of the anti-PSA antibody-solid phased substrate (Preparation Example 1).

The results of preparing and measuring the measurement samples by the above-described methods are shown in Table 5 below. The results shown in Table 5 are actually measured values. The signal values of the AFP-added sera denote those of "AFP-originated signal value+background"

TABLE 5

Relationship between Enzyme Treatment in Solution and Background (AFP)

|  | Mannosidase (−) | Mannosidase (+) |
|---|---|---|
| Pooled serum 1 (AFP-free) | 220,000 | 150,000 |
| Pooled serum 2 (AFP-free) | 240,000 | 180,000 |
| Pooled serum 3 (AFP-free) | 256,000 | 170,200 |
| Pooled serum 4 (AFP-free) | 220,000 | 193,000 |
| Pooled serum 5 (AFP-free) | 230,000 | 170,000 |
| Pooled serum 1 (with addition of AFP-L3 at 1.0 ng/mL) | 940,400 | 800,100 |
| Pooled serum 2 (with addition of AFP-L3 at 1.0 ng/mL) | 994,000 | 880,400 |
| Pooled serum 3 (with addition of AFP-L3 at 1.0 ng/mL) | 998,300 | 911,100 |
| Pooled serum 4 (with addition of AFP-L3 at 1.0 ng/mL) | 1,002,000 | 916,000 |
| Pooled serum 5 (with addition of AFP-L3 at 1.0 ng/mL) | 931,300 | 917,000 |

It was confirmed that, in the measurement samples treated with mannosidase, the values of the respective AFP-free pooled sera (background) were reduced to a level of about ¾ as compared to almost all of the untreated samples. It was also confirmed that, in this case, the AFP-L3-added sera had almost no difference in their measured values.

In addition, while the average S/N ratio value (signal value of AFP-L3-added serum/signal value of corresponding AFP-free serum) of 5 samples was 4.18 in the untreated samples, it was increased to 5.14 in the mannosidase-treated samples, revealing that the detection sensitivity was increased.

Example 5

(Measurement of AFP in Serum Sample (2))

Each sample was subjected to an enzyme treatment with mannosidase and then allowed to react with the anti-AFP antibody-solid phased substrate (Preparation Example 2). Thereafter, the resulting sample was brought into contact with the fluorescently-labeled LCA lectin (Production Example 2).

More particularly, measurement of AFP in each sample was carried out in the same manner as in Example 2, except that: mannosidase derived from *Canavalia ensiformis* (GKX-5010, manufactured by ProZyme, Inc.) was used in place of the galactosidase; the fluorescently-labeled LCA lectin (Production Example 2) was used in place of the fluorescently-labeled WFA lectin (Production Example 1); and the anti-AFP antibody-solid phased substrate (Preparation Example 2) was used in place of the anti-PSA antibody-solid phased substrate (Preparation Example 1).

The results of measuring the measurement samples by the above-described method are shown in Table 6 below. The results shown in Table 6 are actually measured values. The signal values of the AFP-added sera denote those of "AFP-originated signal value+background".

TABLE 6

Relationship between Enzyme Treatment in Solution and Background (AFP)

|  | Mannosidase (−) | Mannosidase (+) |
|---|---|---|
| Pooled serum 1 (AFP-free) | 123,000 | 50,200 |
| Pooled serum 2 (AFP-free) | 140,000 | 80,900 |
| Pooled serum 3 (AFP-free) | 143,000 | 59,200 |
| Pooled serum 4 (AFP-free) | 141,000 | 76,300 |
| Pooled serum 5 (AFP-free) | 135,000 | 70,300 |
| Pooled serum 1 (with addition of AFP-L3 at 1.0 ng/mL) | 843,400 | 700,300 |
| Pooled serum 2 (with addition of AFP-L3 at 1.0 ng/mL) | 894,000 | 781,300 |
| Pooled serum 3 (with addition of AFP-L3 at 1.0 ng/mL) | 885,300 | 800,100 |
| Pooled serum 4 (with addition of AFP-L3 at 1.0 ng/mL) | 923,000 | 799,300 |
| Pooled serum 5 (with addition of AFP-L3 at 1.0 ng/mL) | 836,300 | 817,300 |

It was confirmed that, in the measurement samples treated with mannosidase, the values of the respective AFP-free pooled sera (background) were reduced to a level of about ½ as compared to almost all of the untreated samples. It was also confirmed that, in this case, the AFP-L3-added sera had almost no difference in their measured values.

In addition, while the average S/N ratio value (signal value of AFP-L3-added serum/signal value of corresponding AFP-free serum) of 5 samples was 6.43 in the untreated samples, it was increased to 11.84 in the mannosidase-treated samples, revealing that the detection sensitivity was increased.

Example 6

(Measurement of AFP in Serum Sample (3))

Next, a method of performing an enzyme treatment on a substrate will also be described.

After allowing each sample to react with the anti-AFP antibody-solid phased substrate (Preparation Example 2), the resulting sample was subjected to an enzyme treatment with mannosidase and then brought into contact with the fluorescently-labeled LCA lectin (Production Example 2).

More particularly, measurement of AFP in each sample was carried out in the same manner as in Example 3, except that: mannosidase derived from *Canavalia ensiformis* (GKX-5010, manufactured by ProZyme, Inc.) was used in place of the galactosidase; the fluorescently-labeled LCA lectin (Production Example 2) was used in place of the fluorescently-labeled WFA lectin (Production Example 1); and the anti-AFP antibody-solid phased substrate (Preparation Example 2) was used in place of the anti-PSA antibody-solid phased substrate (Preparation Example 1).

The results are shown in Table 7 below. The results shown in Table 7 are actually measured values. The signal values of the AFP-added sera denote those of "AFP-originated signal value+background".

TABLE 7

Relationship between Enzyme Treatment on Substrate and Background (AFP)

| | Mannosidase (−) | Mannosidase (+) |
|---|---|---|
| Pooled serum 1 (AFP-free) | 102,100 | 40,200 |
| Pooled serum 2 (AFP-free) | 104,400 | 39,900 |
| Pooled serum 3 (AFP-free) | 105,000 | 51,000 |
| Pooled serum 4 (AFP-free) | 129,000 | 35,300 |
| Pooled serum 5 (AFP-free) | 118,500 | 46,300 |
| Pooled serum 1 (with addition of AFP-L3 at 1.0 ng/mL) | 884,100 | 790,300 |
| Pooled serum 2 (with addition of AFP-L3 at 1.0 ng/mL) | 929,400 | 896,300 |
| Pooled serum 3 (with addition of AFP-L3 at 1.0 ng/mL) | 935,300 | 896,900 |
| Pooled serum 4 (with addition of AFP-L3 at 1.0 ng/mL) | 869,200 | 693,300 |
| Pooled serum 5 (with addition of AFP-L3 at 1.0 ng/mL) | 868,800 | 795,300 |

It was confirmed that, in the measurement samples treated with mannosidase on the substrate, the values of the respective AFP-free pooled sera (background) were reduced to a level of about 2/5 as compared to almost all of the untreated samples.

In addition, while the average S/N ratio value (signal value of AFP-L3-added serum/signal value of corresponding AFP-free serum) of 5 samples was 8.11 in the untreated samples, it was increased to 19.31 in the mannosidase-treated samples, revealing that the detection sensitivity was increased.

As shown in the above Examples 4 to 6, it was confirmed that non-specific binding signal generated in the measurement system by serum component can be suppressed by cleaving mannose on serum glycoprotein and that the sensitivity for specifically detecting the fucose sugar chain structure on AFP is consequently improved.

Moreover, as a result of comparing Examples 5 and 6, it was confirmed that the enzyme treatment exerts superior effect when performed on an antibody-immobilized substrate with a certain level of focus on the treatment subject than when the enzyme is made to act in a solution containing a large amount of serum proteins.

In the above Examples, an embodiment where various solutions are circulated in a SPFS measurement apparatus was described as an example; however, a solution is not necessarily required to be circulated and a variety of modifications, such as an embodiment where a solution is continuously transferred in one direction, an embodiment where a solution is transferred in a reciprocating manner in both directions and an embodiment where a solution of a prescribed amount is transferred and then retained for a prescribed period, can be applied within the scope of the objects of the present invention.

DESCRIPTION OF SYMBOLS

10: Quantitative measurement apparatus
12: Dielectric member
12a: Upper surface
12b: Side surface
12c: Side surface
14: Metal film
14a: Upper surface
16: Sensor chip
18: Sensor chip mounting section
20: Light source
22: Incoming light
24: Metal film-reflected light
26: Light-receiving means
28: SPR-measuring section
30: Fluorescence
32: Light-detecting means
34: SPFS measurement section
36: Fine flow path
38: Sensor section
40: Quantitative calculation means
44: Antigen-binding molecule (ligand)
46: Antigen to be detected (analyte)
46a: Antigen having a particular sugar chain
46b: Sugar chain excluding a particular sugar chain, to which a lectin does not bind
46c: Particular sugar chain
46d: Sugar chain excluding a particular sugar chain, to which a lectin can bind
48: Fluorescently-labeled lectin (probe)
50: Non-specifically adsorbing serumglycoprotein in serum
50a: Protein having a sugar chain
51: Non-specifically adsorbing serum glycoprotein whose terminal sugar chain is cleaved with an enzyme
52: Non-specifically adsorbing glycolipid in serum
52a: Lipid having a sugar chain
53: Non-specifically adsorbing glycolipid whose terminal sugar chain is cleaved with an enzyme
60: Lectin binding to plural kinds of sugar chains including a specific sugar chain
61: Label
70: Glycohydrolase
80: Support
81: Reaction system

The invention claimed is:

1. A method of detecting an analyte having a target sugar chain in a sample containing one or more contaminants, said method comprising:
   (a) a step of bringing a labeled lectin into contact with said sample containing said one or more contaminants, to allow said lectin to bind to said target sugar chain, said one or more contaminants being one or more glycoproteins or glycolipids other than said analyte, and said lectin being capable of binding to said target sugar chain and at least one other sugar chain;

(b) a step of bringing a glycohydrolase into contact with said sample, said glycohydrolase being capable of cleaving said at least one other sugar chain to which said lectin is capable of binding, said at least one other sugar chain being at least one sugar chain other than said target sugar chain; and (c) a step of detecting said labeled lectin to detect said analyte which binds to said lectin, wherein step (c) is carried out after steps (a) and (b), and wherein a combination of said analyte, said lectin, and said glycohydrolase is any of the following combinations of (1) to (8):

(1) said analyte is prostate-specific antigen, said lectin is *Wisteria floribunda* lectin, and said glycohydrolase is galactosidase;

(2) said analyte is prostate-specific antigen, said lectin is soybean lectin, and said glycohydrolase is galactosidase;

(3) said analyte is prostate-specific antigen, said lectin is *Trichosanthes japonica* lectin (TJA-II), and said glycohydrolase is fucosidase;

(4) said analyte is α-fetoprotein, said lectin is *Lens culinaris* lectin, and said glycohydrolase is mannosidase;

(5) said analyte is carcinoembryonic antigen, said lectin is *Trichosanthes japonica* lectin (TJA-I), and said glycohydrolase is galactosidase;

(6) said analyte is α-fetoprotein, said lectin is *Aleuria aurantia* lectin, and said glycohydrolase is fucosidase;

(7) said analyte is CA125 antigen, said lectin is wheat germ lectin, and said glycohydrolase is N-acetylglucosaminidase; and (8) said analyte is thyroglobulin, said lectin is *Canavalia ensiformis* lectin, and said glycohydrolase is glucosidase.

2. The method of detecting an analyte according to claim 1, further comprising, before said step (c), a step (d) of bringing said sample into contact with a support on which a molecule binding to said analyte is immobilized.

3. The method of detecting an analyte according to claim 2, wherein said step (d) is carried out before steps (a) and (b).

4. The method of detecting an analyte according to claim 2, wherein steps (a) and (b) are carried out before said step (d).

5. The method of detecting an analyte according to claim 1, wherein steps (a) and (b) are carried out simultaneously.

6. The method of detecting an analyte according to claim 1, wherein step (a) is carried out before said step (b).

7. The method of detecting an analyte according to claim 1, wherein step (b) is carried out before said step (a).

8. The method of detecting an analyte according to claim 2, wherein step (d) is carried out after said step (a) and before step (b).

9. The method of detecting an analyte according to claim 2, wherein step (d) is carried out after step (b) and before step (a).

10. The method of detecting an analyte according to claim 1, wherein:
said analyte is prostate-specific antigen;
said lectin is *Wisteria floribunda* lectin; and
said glycohydrolase is galactosidase.

11. The method of detecting an analyte according to claim 1, wherein:
said analyte is prostate-specific antigen;
said lectin is soybean lectin; and
said glycohydrolase is galactosidase.

12. The method of detecting an analyte according to claim 1, wherein:
said analyte is prostate-specific antigen;
said lectin is *Trichosanthes japonica* lectin (TJA-II); and
said glycohydrolase is fucosidase.

13. The method of detecting an analyte according to claim 1, wherein:
said analyte is α-fetoprotein;
said lectin is *Lens culinaris* lectin; and
said glycohydrolase is mannosidase.

14. The method of detecting an analyte according to claim 1, wherein:
said analyte is carcinoembryonic antigen;
said lectin is *Trichosanthes japonica* lectin (TJA-I); and
said glycohydrolase is galactosidase.

15. The method of detecting an analyte according to claim 1, wherein:
said analyte is α-fetoprotein;
said lectin is *Aleuria aurantia* lectin; and
said glycohydrolase is fucosidase.

16. The method of detecting an analyte according to claim 1, wherein:
said analyte is CA 125 antigen;
said lectin is wheat germ lectin; and
said glycohydrolase is N-acetylglucosaminidase.

17. The method of detecting an analyte according to claim 1, wherein:
said analyte is thyroglobulin;
said lectin is *Canavalia ensiformis* lectin; and
said glycohydrolase is glucosidase.

18. The method of detecting an analyte according to claim 1, wherein the label of the lectin comprises at least one of a fluorescent dye, an enzyme, a coenzyme, a chemiluminescent substance, and a radioactive substance.

* * * * *